United States Patent
Park et al.

(10) Patent No.: US 9,273,306 B2
(45) Date of Patent: *Mar. 1, 2016

(54) AUTOMATIC NECLEIC ACID PURIFICATION APPARATUS AND METHOD FOR AEROSOL-PROTECTING

(75) Inventors: Han Oh Park, Daejeon (KR); Byung Rae Jeong, Daejeon (KR); Kwon Sic Kim, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 86 days.

This patent is subject to a terminal disclaimer.

(21) Appl. No.: 13/885,556

(22) PCT Filed: Nov. 18, 2011

(86) PCT No.: PCT/KR2011/008845
§ 371 (c)(1),
(2), (4) Date: May 15, 2013

(87) PCT Pub. No.: WO2012/067465
PCT Pub. Date: May 24, 2012

(65) Prior Publication Data
US 2013/0236903 A1    Sep. 12, 2013

(30) Foreign Application Priority Data

Nov. 18, 2010  (KR) .................. 10-2010-0114970

(51) Int. Cl.
*C12Q 1/68*    (2006.01)
*B01L 3/00*    (2006.01)
*C12N 15/10*   (2006.01)

(52) U.S. Cl.
CPC .......... *C12N 15/1013* (2013.01); *C12Q 1/6802* (2013.01)

(58) Field of Classification Search
CPC ............................ C12Q 1/6802; B01L 3/0275
USPC ............................................ 435/6.1; 422/501
See application file for complete search history.

(56) References Cited

U.S. PATENT DOCUMENTS

| 5,647,994 A | 7/1997 | Tuunanen et al. |
| 5,702,950 A | 12/1997 | Tajima |
| 5,897,783 A | 4/1999 | Howe et al. |

(Continued)

FOREIGN PATENT DOCUMENTS

| EP | 0479448 | 4/1992 |
| KR | 10-0720044 B1 | 5/2007 |

(Continued)

*Primary Examiner* — Betty Forman
(74) *Attorney, Agent, or Firm* — Paratus Law Group, PLLC

(57) ABSTRACT

Disclosed is an automatic nucleic acid purification apparatus which can prevent pollution due to aerosol generated from a biological sample containing high concentration target nucleic acid when the biological sample containing the high concentration target nucleic acid is mixed with other biological sample containing low concentration target nucleic acid or not containing the target nucleic acid. Further, disclosed is an automatic nucleic acid purification apparatus which can be applied to all kinds of nucleic acid purification equipments for purifying a plurality of biological samples using a magnet rode or a multi-pipette block moving in two or three axial directions, and which can minimize pollution due to the aerosol generated from the biological sample containing high concentration target nucleic acid and also can obtain accurate results.

12 Claims, 17 Drawing Sheets

(56) References Cited

U.S. PATENT DOCUMENTS

| | | |
|---|---|---|
| 6,187,270 B1 | 2/2001 | Schmitt et al. |
| 6,231,814 B1 | 5/2001 | Tajima |
| 2003/0215364 A1* | 11/2003 | Aviles et al. .................. 422/63 |
| 2007/0092403 A1 | 4/2007 | Wirbisky et al. |
| 2009/0130679 A1 | 5/2009 | Wu et al. |
| 2010/0285996 A1* | 11/2010 | Tajima ........................... 506/27 |
| 2011/0009608 A1 | 1/2011 | Kim et al. |
| 2013/0043191 A1* | 2/2013 | Park et al. ..................... 210/695 |
| 2013/0130369 A1* | 5/2013 | Wilson et al. .............. 435/289.1 |

FOREIGN PATENT DOCUMENTS

| | | |
|---|---|---|
| KR | 10-2011-0121588 A | 11/2011 |
| WO | WO 2009-125971 A2 | 10/2009 |

* cited by examiner

AUTOMATIC NECLEIC ACID PURIFICATION APPARATUS AND METHOD FOR AEROSOL-PROTECTING

CROSS REFERENCE TO PRIOR APPLICATION

This application is a National Stage Patent Application of PCT International Patent Application No. PCT/KR2011/008845 (filed on Nov. 18, 2011) under 35 U.S.C. §371, which claims priority to Korean Patent Application No. 10-2010-0114970 (filed on Nov. 18, 2010), which are all hereby incorporated by reference in their entirety.

TECHNICAL FIELD

The present invention relates to an automatic nucleic acid purification apparatus, and more particularly to an automatic nucleic acid purification apparatus which can prevent pollution due to aerosol generated from a biological sample containing high concentration target nucleic acid when the biological sample containing the high concentration target nucleic acid is mixed with other biological sample containing low concentration target nucleic acid or not containing the target nucleic acid.

The present invention relates to an automatic nucleic acid purification apparatus which can be applied to all kinds of nucleic acid purification equipments for purifying a plurality of biological samples using a magnet rode or a multi-pipette block moving in two or three axial directions, and which can minimize pollution due to the aerosol generated from the biological sample containing high concentration target nucleic acid and also can obtain accurate results.

BACKGROUND ART

An automatic nucleic acid purification apparatus is mainly used to isolate nucleic acid from a biological sample. This is caused by that a quantitative test can be high-sensitively and precisely performed with respect to target pathogenic bacteria of from 10 or less to one billion using real-time quantitative PCR. However, the nucleic acid purification is simultaneously performed with respect to multiple biological samples. Therefore, in case that the purification is simultaneously performed with respect to a biological sample containing high concentration target pathogenic bacteria and another biological sample not containing target nucleic acid, a false positive may be occurred by pollution due to aerosol. For example, in case of purifying target nucleic acids in a biological sample containing one billion viruses per 1 ml, even when another biological sample is polluted with a hundred millionth ml of the aerosol generated from the biological sample, i.e., 1 pl (picoliter) of aerosol, the false positive may be occurred.

Generally, a material to which nucleic acid is selectively attached is used in purifying nucleic acid. There are a method using a membrane and a method using magnetic particles. Typically, the method using magnetic particles is more widely used. In this method, instead of a vacuum manner in which it is easy to generate the aerosol, biochemistry substance is rapidly attached to magnetic particles suspended in a solution, and the magnetic particles to which the target substance is attached is cohered by magnetic field, and then the solution is removed. There has been developed various relevant automatic equipments.

According to an attaching manner of the magnetic particles, this is classified into a method of attaching the magnetic particles to a pipette, a method of attaching the magnetic particles to a tube in which a magnet rod is inserted, and a method of the magnetic particles to a multi-well plate.

Recently, an automatic method using a pipette is wisely used. In U.S. Pat. No. 5,647,994 (Labsystems Co., Ltd.), there have been described various methods of separating magnetic particles using a disposable pipette. Also, in U.S. Pat. Nos. 5,702,950 and 6,231,814 (Precision System Science Co., Ltd.), magnetic particles are attached to a pipette, and a basic principle thereof is the same as in U.S. Pat. No. 5,647,994. A difference between them is that a magnet is attached and detached in one direction of the pipette and thus magnetic field is controlled in one direction of a pipette tip. This patent is characterized in that a magnetic substance attracting/releasing control method comprises the steps of: providing a pipette device having a liquid suction line including a liquid inlet end for sucking liquid containing the magnetic substance from a container and discharging the liquid through the liquid inlet end, and a magnet body or magnet bodies being detachably fitted to an external peripheral surface of the liquid suction line of the pipette device; the pipette device providing attracting/releasing control by absorbing and maintaining the magnetic substance contained in the liquid and attracted to the liquid suction line due to magnetism in the magnet body or bodies on an internal surface of the liquid suction line, the magnetic substance being maintained on the internal surface of the pipette device and also by releasing the magnetic substance from the liquid suction line by means of interrupting effect by magnetism in the magnet body or bodies so that the substance is discharged together with the liquid to outside of the liquid suction line through the liquid inlet end.

In U.S. Pat. No. 6,187,2070 (Roche Diagnostics GmbH), there is disclosed a method of separation of magnetic particles, in which a permanent magnet is approached to a disposable tip so as to adhere the magnetic particles, thereby separating the magnetic particles from a solution. To this end, an apparatus for separation of the magnetic particles includes a pipette connected to a pump, a magnet, and a means for moving the magnet to the pipette side or the opposite side thereof. Herein, there is provided the method of separating the magnetic particles from the solution and then suspending them in another solution. However, one of the uppermost limits is that a lower portion of the pipette is clogged with the magnetic particles, and thus the results become inaccurate.

There has been proposed a method for nucleic acid purification, in which magnetic particles are attached to a detachable magnet rod and then moved to various solutions for nucleic acid purification. To this end, there has been developed various models such as Maxwell 16™ manufactured by Promega Co., Ltd and King Fisher™ manufactured by Thermo Co., Ltd. In these systems, since the solution is stirred by moving up and down a tube in which a rod for collecting the magnetic particles is inserted, the entire part of the tube is smeared with the solution containing nucleic acid.

In a conventional method, a reaction is performed in a container in which a biological sample is received, and magnetic particles are attached to a desired place, and then the purification is carried out. By Gen-Probe, Inc., there has been proposed a method for separating particles, which are attracted by magnetic field, using a separation rack. In U.S. Pat. No. 5,897,783 (Amersham International plc), there has been disclosed a method of moving a doughnut-shaped permanent magnet in a vertical direction to a container and thus switching magnetic field. In EP0479448 (Beckman instruments, Inc), there has been disclosed an automatic purification apparatus in which a sample containing magnetic materials is separated using a magnetic plate. The magnetic plate is formed with a plurality of holes through which a container can be passed, and the automatic purification apparatus also includes a means for moving up and down the magnetic plate. In case that magnetic particles are attached to a bottom portion, mixing of a magnetic particle suspension, a sample and a solution is occurred in a dispensable pipette, and thus the solution containing nucleic acid is smeared on an outer surface of the pipette.

When performing purification of biological substances, all of the above-mentioned methods essentially include a step of moving a pipette or a tube, on which the solution containing nucleic acid is smeared due to binding of Lysis and magnetic particles, a cleaning reaction and the like, to another space. In this step, since a vortex of air is generated on the outer surface of the dispensable pipette or the purification tube, pollution due to aerosol is unavoidable.

However, in the automatic purification apparatuses which have been developed till now, consideration for efficiently preventing the generation of aerosol is yet insignificant. As a pollution preventing system which has been developed till now, a solution drip guard for preventing solution drips from a dispensable pipette is applied to Exiprep 16 Pro manufactured by Bioneer Corporation and to MagnaPure 96 manufactured by Roche. But even though it is possible to prevent the solution drips from the pipette, it is not possible to prevent the aerosol generated from the solution containing nucleic acid attached to the hydrophobic surface of the pipette by a vortex of air generated when the pipette is moved. Therefore, it is inevitable that the aerosol is generated during a series of processes for separating target nucleic acid from a biological sample solution, and particularly, it is not possible to avoid false positive pollution in PCR due to the aerosol generated from the solution containing high concentration nucleic acid.

The present invention is to minimize the generation of aerosol generated from fine drips attached on the outer surface of the pipette by air flow and thus to minimize a cross pollution.

DISCLOSURE OF INVENTION

Technical Problem

An object of the present invention is to provide an automatic nucleic acid purification apparatus in which, in order to fundamentally prevent the generation of aerosol due to a vortex of air when a pipette or a magnet rod tube on which a solution containing nucleic acid is attached is horizontally moved, the pipette or the magnet is moved after a closed space for minimizing air flow is at a portion of the pipette or the magnet rod tube, on which the solution containing nucleic acid is attached, so that the aerosol is not generated from the surface of the pipette or the magnet, and after the movement, the pipette or the magnet is freely moved up and down so as to perform the nucleic acid purification without reciprocal crossing over.

Further, another object of the present invention is to provide an automatic nucleic acid purification apparatus which can prevent pollution of a plurality of unit wells of a multi-well plate due to undesirable solution drips from the plurality of pipettes.

Solution to Problem

To achieve the object of the present invention, the present invention provides an automatic purification apparatus for isolating target nucleic acids from a plurality of biological samples and also for aerosol-protecting, including a purification block 110 in which a plurality of pipettes P or a plurality of magnet rod tubes are installed and also which is disposed to be moved vertically and horizontally; a solution drip tray 1050 which is disposed so as to be spaced apart from lower ends of the plurality of pipettes P or the plurality of magnet rod tubes and also to be movable to a position where the solution drip tray 1050 can receive solution drips from the plurality of pipettes P or the plurality of magnet rod tubes and another position where the solution drip tray 1050 can avoid in contact with plurality of pipettes P or the plurality of magnet rod tubes when the purification block 110 is moved down; and an aerosol prevention part 1070 which is formed so as to cover portions of the plurality of pipettes P or the plurality of magnet rod tubes, which are smeared with a solution containing the target nucleic acid, by being tightly contacted with the solution drip tray 1050 which is located at the position where the solution drip tray 1050 can receive the solution drips, so that the portions of the plurality of pipettes P or the plurality of magnet rod tubes, which are smeared with the solution containing the target nucleic acid, are shut off from the outside.

Preferably, the solution drip tray 1050 is formed into a flat plate shape, and the aerosol prevention part 1070 is installed at a certain vertical position so that an upper inner surface of the aerosol prevention part 1070 is tightly contacted with the purification block 110 and a lower end thereof is tightly contacted with the solution drip tray 1050 when the purification block 110 is moved upward.

Preferably, the aerosol prevention part 1070 is formed into a rectangular box shape and comprises a first side plate 73-1 for aerosol prevention part, a third side plate 73-2 for aerosol prevention part, which is disposed to be faced with the first side plate 73-1 for aerosol prevention part, a second side plate 75-1 for aerosol prevention part, of which both side ends are connected with the first and third side plates 73-1 and 73-2 for aerosol prevention part, and a fourth side plate 75-2 for aerosol prevention part, which is disposed to be spaced apart from the second side plate 75-1 for aerosol prevention part and of which both side ends are connected with the first and third side plates 73-1 and 73-2 for aerosol prevention part and is located at higher position than a lower end of the second side plate 75-1 for aerosol prevention part, and the solution drip tray 1050 comprises a lower plate 51 for solution drip tray, a first tightly-contacting plate 53-1 for solution drip tray, which is uprightly disposed at the lower plate 51 for solution drip tray so that an inner side surface of the first tightly-contacting plate 53-1 for solution drip tray is tightly contacted with an outer surface of the first side plate 73-1 for aerosol preventing part, a second tightly-contacting plate 55-1 for solution drip tray, which is uprightly disposed at the lower plate 51 for solution drip tray so that an outer side surface of the second tightly-contacting plate 55-1 for solution drip tray is tightly contacted with an inner surface of the second side plate 75-1 for aerosol preventing part, a third tightly-contacting plate 53-2 for solution drip tray, which is uprightly disposed at the lower plate 51 for solution drip tray so that an inner side surface of the third tightly-contacting plate 53-2 for solution drip tray is tightly contacted with an outer surface of the third side plate 73-2 for aerosol preventing part, and a fourth tightly-contacting plate 55-2 for solution drip tray, which is uprightly disposed at the lower plate 51 for solution drip tray so that an inner side surface of the fourth tightly-contacting plate 55-2 for solution drip tray is tightly contacted with an outer surface of the fourth side plate 75-2 for aerosol preventing part.

Preferably, the solution drip tray 1050 is formed into a flat plate shape, and the aerosol prevention part 1070 is formed into a box shape and disposed to be moved to up and down directions of the purification block 110, such that an upper inner surface thereof is tightly contacted with the purification block 110 and a lower end thereof is tightly contacted with the solution drip tray 1050 when the aerosol prevention part 1070 is moved down.

Preferably, the solution drip tray 1050 comprises a lower plate 251 for solution drip tray and a side plate 253 for solution drip tray, which is uprightly disposed at an edge portion of the lower plate 251 for solution drip tray so as to form an longitudinally "L"-shaped cross section together with the lower plate 251 for solution drip tray, and the aerosol prevention part 1070 is disposed to be moved to up and down directions of the purification block 110, such that an upper inner surface thereof is tightly contacted with the purification block 110 and a lower end thereof is tightly contacted with the solution drip tray 1050 when the aerosol prevention part 1070 is moved down, and also the aerosol prevention part 1070 has an transversely "U"-shaped cross section so that both side ends of an opened circumferential surface thereof are tightly contacted with the side plate 253 for solution drip tray.

Preferably, the solution drip tray 1050 comprises a lower plate 251 for solution drip tray and a side plate 253 for solution drip tray, which is uprightly disposed at an edge portion of the lower plate 251 for solution drip tray so as to form an longitudinally "L"-shaped cross section together with the lower plate 251 for solution drip tray, and the aerosol prevention part 1070 is installed at a certain vertical position to have an transversely "U"-shaped cross section, such that an upper inner surface thereof is tightly contacted with the purification block 110 and a lower end thereof is tightly contacted with the lower plate 251 for solution drip tray and both side ends of an opened circumferential surface thereof are tightly contacted with the side plate 253 for solution drip tray, when the purification block 110 is moved upward.

Preferably, the solution drip tray 1050 comprises a lower plate 351 for solution drip tray and side plates 353-1 and 353-2 for solution drip tray, which are uprightly disposed at both edge portions of the lower plate 351 for solution drip tray so as to form an longitudinally "U"-shaped cross section together with the lower plate 351 for solution drip tray, and the aerosol prevention part 1070 is disposed to be moved to up and down directions of the purification block 110, and comprises two side plates 373-1 and 373-2 for aerosol prevention part which are disposed at both opposed side surfaces of the purification block 110, such that upper inner surfaces thereof are tightly contacted with the purification block 110 and lower ends thereof are tightly contacted with the lower plate 351 for solution drip tray and both sides ends thereof are tightly contacted with the side plates 353-1 and 353-2 for solution drip tray, when the aerosol prevention part 1070 is moved down.

Preferably, the solution drip tray 1050 comprises a lower plate 351 for solution drip tray and side plates 353-1 and 353-2 for solution drip tray, which are uprightly disposed at both edge portions of the lower plate 351 for solution drip tray so as to form an longitudinally "U"-shaped cross section together with the lower plate 351 for solution drip tray, and the aerosol prevention part 1070 comprises two side plates 373-1 and 373-2 for aerosol prevention part which are disposed at a certain vertical position so as to be faced with each other with the purification block 110 being interposed therebetween, such that upper inner surfaces thereof are tightly contacted with the purification block 110 and lower ends thereof are tightly contacted with the lower plate 351 for solution drip tray and both sides ends thereof are tightly contacted with the side plates 353-1 and 353-2 for solution drip tray, when the purification block 110 is moved up.

Preferably, the solution drip tray 1050 is disposed so as to be moved horizontally, such that the side plates 253, 353-1 and 353-2 for solution drip tray are moved along the same vertical surfaces, in order to minimize an air flow when the solution drip tray 1050 is moved to a position where the solution drip tray 1050 can receive solution drips from the plurality of pipettes P or the plurality of magnet rod tubes and another position where the solution drip tray 1050 can avoid in contact with plurality of pipettes P or the plurality of magnet rod tubes upon downward movement of the purification block 110.

Preferably, the solution drip tray 1050 is formed with an insertion groove 151-G in which a lower end of the aerosol prevention part 1070 is inserted.

Preferably, the solution drip tray 1050 is formed into a flat plate shape, and the aerosol prevention part 1070 is disposed at a lower side of the purification block 110 so as to be moved to up and down directions of the purification block 110, and also the aerosol prevention part 1070 comprises an aerosol prevention tube supporting plate 471 formed with a plurality of through-holes 471-H which a plurality of pipettes P or a plurality of magnet rod tubes are inserted therein and passed therethrough, and a plurality of aerosol prevention tube 473 which are communicated with the plurality of through-holes 471-H so as to cover portions of the plurality of pipettes P or the plurality of magnet rod tubes, which are smeared with a solution containing the target nucleic acid, when the aerosol prevention tube supporting plate 471 is moved down, and which are extended to a lower side of the aerosol prevention tube supporting plate 471 so that lower ends thereof are tightly contacted with the solution drip tray 1050.

Preferably, the solution drip tray 1050 is formed into a flat plate shape, and the aerosol prevention part 1070 is installed at a certain vertical position of a lower side of the purification block 110, and also the aerosol prevention part 1070 comprises an aerosol prevention tube supporting plate 471 formed with a plurality of through-holes 471-H which a plurality of pipettes P or a plurality of magnet rod tubes are inserted therein and passed therethrough, and a plurality of aerosol prevention tubes 473 which are communicated with the plurality of through-holes 471-H so as to cover portions of the plurality of pipettes P or the plurality of magnet rod tubes, which are smeared with a solution containing the target nucleic acid, and which are extended to a lower side of the aerosol prevention tube supporting plate 471 so that lower ends thereof are tightly contacted with the solution drip tray 1050.

Preferably, the solution drip tray 1050 is formed into a flat plate shape, and the aerosol prevention part 1070 is disposed at a lower side of the purification block 110 so as to be moved to up and down directions of the purification block 110, and also the aerosol prevention part 1070 comprises an aerosol prevention tube supporting plate 571 formed with a plurality of through-holes 571-H which a plurality of pipettes P or a plurality of magnet rod tubes are inserted therein and passed therethrough, a plurality of aerosol prevention tubes 573 which are communicated with the plurality of through-holes 571-H so as to cover portions of the plurality of pipettes P or the plurality of magnet rod tubes, which are smeared with a solution containing the target nucleic acid, when the aerosol prevention tube supporting plate 571 is moved down, and which are extended to a lower side of the aerosol prevention tube supporting plate 571, and an aerosol prevention container 575 which covers the plurality of aerosol prevention tubes 573 and which is extended to a lower side of the aerosol prevention tube supporting plate 571 so that a lower end thereof is tightly contacted with the solution drip tray 1050 when the aerosol prevention tube supporting plate 571 is moved down.

Preferably, the solution drip tray 1050 is formed into a flat plate shape, and the aerosol prevention part 1070 is installed at a certain vertical position of a lower side of the purification block 110, and also the aerosol prevention part 1070 comprises an aerosol prevention tube supporting plate 571 formed with a plurality of through-holes 571-H which a plurality of pipettes P or a plurality of magnet rod tubes are inserted therein and passed therethrough, a plurality of aerosol prevention tubes 573 which are communicated with the plurality of through-holes 571-H so as to cover portions of the plurality of pipettes P or the plurality of magnet rod tubes, which are smeared with a solution containing the target nucleic acid, when the aerosol prevention tube supporting plate 571 is moved down, and which are extended to a lower side of the aerosol prevention tube supporting plate 571, and an aerosol prevention container 575 which covers the plurality of aerosol prevention tubes 573 and which is extended to a lower side of the aerosol prevention tube supporting plate 571 so that a lower end thereof is tightly contacted with the solution drip tray 1050 when the aerosol prevention tube supporting plate 571 is moved down.

Preferably, the solution drip tray 1050 is formed into a flat plate shape, and the aerosol prevention part 1070 is disposed at a lower side of the purification block 110 so as to be moved up and down, and also the aerosol prevention part 1070 comprises an aerosol prevention block 671 which is formed with a plurality of through-holes 671-H so as to cover the portions of the plurality of pipettes P or the plurality of magnet rod tubes, which are smeared with a solution containing the target nucleic acid, when the aerosol prevention block 671 is moved down.

Preferably, the solution drip tray 1050 is formed into a flat plate shape, and the aerosol prevention part 1070 is installed at a certain vertical position of a lower side of the purification block 110, and also the aerosol prevention part 1070 comprises an aerosol prevention block 671 which is formed with a plurality of through-holes 671-H so as to cover the portions of the plurality of pipettes P or the plurality of magnet rod tubes, which are smeared with a solution containing the target nucleic acid.

Preferably, the solution drip tray 1050 is formed into a flat plate shape, and the aerosol prevention part 1070 is disposed at a lower side of the purification block 110 so as to be moved up and down, and also the aerosol prevention part 1070 comprises an upper plate 771 for aerosol prevention part formed with a plurality of through-holes 771-H which a plurality of pipettes P or a plurality of magnet rod tubes are inserted therein and passed therethrough, and an aerosol prevention container 775 which is extended from an edge portion of the upper plate 771 for aerosol prevention part to a lower side thereof so as to cover portions of the plurality of pipettes P or the plurality of magnet rod tubes, which are smeared with a solution containing the target nucleic acid, when the upper plate 771 for aerosol prevention part is moved down, so that a lower end thereof is tightly contacted with the solution drip tray 1050.

Preferably, the solution drip tray 1050 is formed into a flat plate shape, and the aerosol prevention part 1070 is installed at a certain vertical position of a lower side of the purification block 110, and also the aerosol prevention part 1070 comprises an upper plate 771 for aerosol prevention part formed with a plurality of through-holes 771-H which a plurality of pipettes P or a plurality of magnet rod tubes are inserted therein and passed therethrough, and an aerosol prevention container 775 which is extended from an edge portion of the upper plate 771 for aerosol prevention part to a lower side thereof so as to cover portions of the plurality of pipettes P or the plurality of magnet rod tubes, which are smeared with a solution containing the target nucleic acid, so that a lower end thereof is tightly contacted with the solution drip tray 1050.

Further, the present invention provides an automatic purification method of isolating target nucleic acids from a plurality of biological samples and also for aerosol-protecting, wherein, when a purification block 110 installed with a plurality of pipettes P or a plurality of magnet rod tubes is moved horizontally, portions of the plurality of pipettes P or the plurality of magnet rod tubes, which are smeared with a solution containing the target nucleic acid, is maintained in a state of being shut off from the outside.

Preferably, the automatic purification method includes a purification block lifting-up step S10 of moving up the purification block 110 so that lower ends of the plurality of pipettes P or the plurality of magnet rod tubes installed in the purification block 110 are located at an upper portion of a lower end of an aerosol prevention part 1070 which is installed at a certain vertical position; a first solution drip tray moving step S20 of moving a solution drip tray 1050 which is formed so as to receive solution drips from the plurality of pipettes P or the plurality of magnet rod tubes to a position where the solution drip tray 1050 can receive solution drips from the plurality of pipettes P or the plurality of magnet rod tubes so as to be tightly contacted with a lower end of the aerosol prevention part 1070 and thus to cover portions of the plurality of pipettes P or the plurality of magnet rod tubes, which are smeared with the solution containing the target nucleic acid, together with the aerosol prevention part 1070; a purification block horizontally-moving step S30 of horizontally moving the purification block 110 in a state that the portions of the plurality of pipettes P or the plurality of magnet rod tubes, which are smeared with the solution containing the target nucleic acid, are shut off from the outside; a second solution drip tray moving step S40 of moving the solution drip tray 1050 to a position that can avoid in contact with plurality of pipettes P or the plurality of magnet rod tubes when the purification block 110 is moved down; and a purification block lifting-down step S50 of lifting down the purification block 110 after the second solution drip tray moving step S40 so that the plurality of pipettes P or the plurality of magnet rod tubes are put in nucleic acid extract solutions.

Preferably, the automatic purification method includes a first solution drip tray moving step S110 of moving a solution drip tray 1050 which is formed so as to receive solution drips from the plurality of pipettes P or the plurality of magnet rod tubes to a lower side of the plurality of pipettes P or the plurality of magnet rod tubes installed in the purification block 110 so as to receive solution drips from the plurality of pipettes P or the plurality of magnet rod tubes; an aerosol prevention part lifting-down step S120 of moving an aerosol prevention part 1070 in a downward direction of the purification block 110 so as to be tightly contacted with the solution drip tray 1050 moved through the first solution drip tray moving step S110 and thus to shut off portions of the plurality of pipettes P or the plurality of magnet rod tubes, which are smeared with the solution containing the target nucleic acid, from the outside together with the solution drip tray 1050; a purification block horizontally-moving step S130 of horizontally moving the purification block 110 in a state that the portions of the plurality of pipettes P or the plurality of magnet rod tubes, which are smeared with the solution containing the target nucleic acid, are shut off from the outside; an aerosol prevention part lifting-up step S140 of moving the aerosol prevention part 1070 to an upper side of the purification block 110 after the purification block horizontally-moving step S130; a second solution drip tray moving step S150 of moving the solution drip tray 1050 to a position that can avoid in contact with plurality of pipettes P or the plurality of magnet rod tubes when the purification block 110 is moved down; and a purification block lifting-down step S160 of lifting down the purification block 110 after the aerosol prevention part lifting-up step S140 and the second solution drip tray moving step S150 so that the plurality of pipettes P or the plurality of magnet rod tubes are put in nucleic acid extract solutions.

Advantageous Effects of Invention

According to the automatic nucleic acid purification apparatus of the present invention, since the pipette or the magnet rod tube is moved only when it is closed so as to be shut off from the outside and then the nucleic acid purification is performed, it is fundamentally prevented that the aerosol is generated due to the vortex of air while the pipette or the magnet rod tube is moved horizontally. Further, since the vortex of air is not generated when the purification block having the plurality of pipettes or the plurality of magnet rod tubes is moved horizontally, the generation of aerosol and the cross pollution are fundamentally prevented.

Further, according to the present invention, it is fundamentally prevented that the plurality of unit wells of the multi-well plate are polluted by the undesirable solution drips from the plurality of pipettes or the plurality of magnet rod tubes.

BRIEF DESCRIPTION OF DRAWINGS

The above and other objects, features and advantages of the present invention will become apparent from the following description of preferred embodiments given in conjunction with the accompanying drawings, in which.

DETAILED DESCRIPTION OF MAIN ELEMENTS

Figure 1:
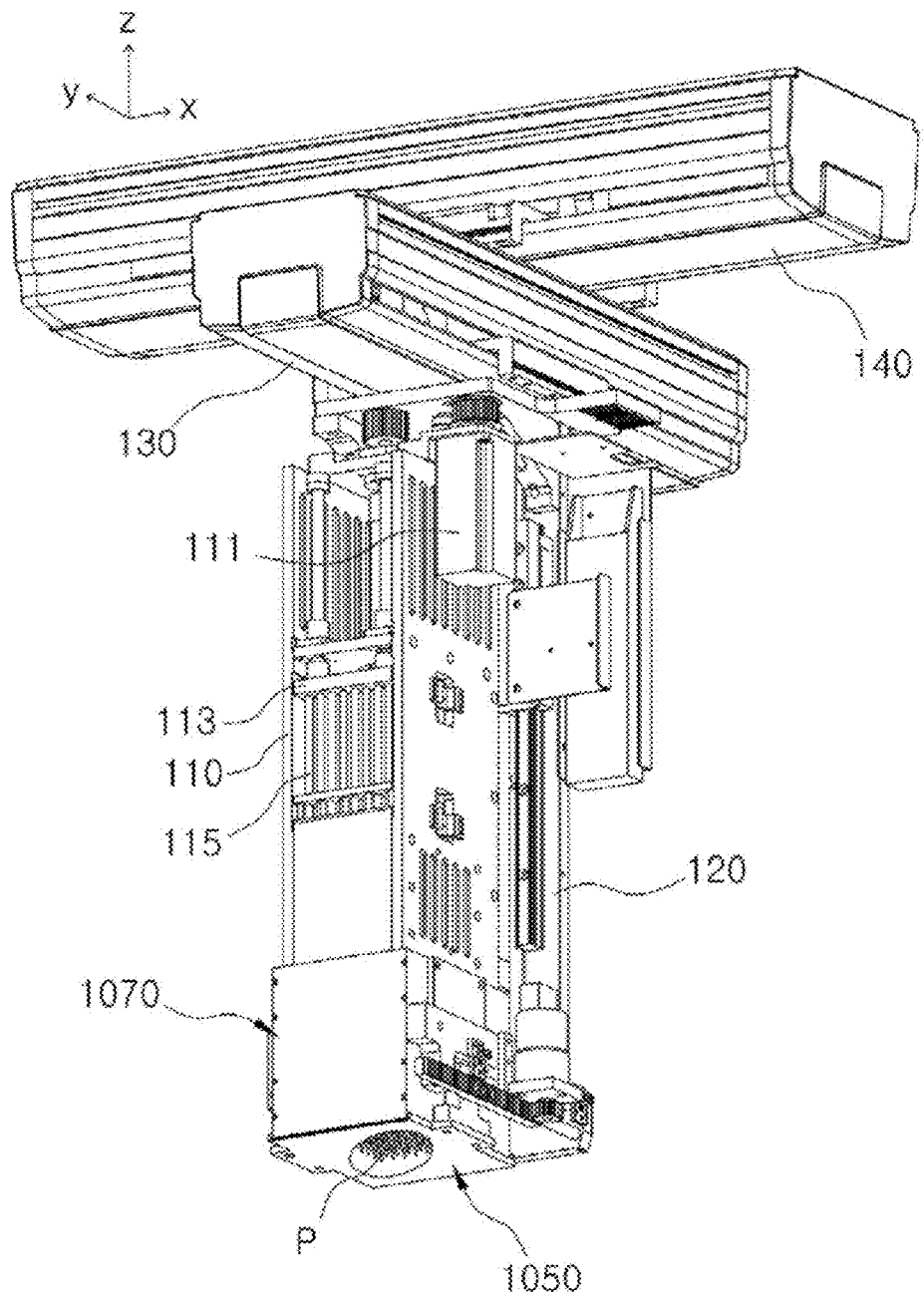
FIGS. 1, 2 and 3 are perspective views showing a first embodiment of the present invention.

110: purification bloc 151-G: insertion groove
251: lower plate for solution drip tray
253: side plate for solution drip tray
351: lower plate for solution drip tray
353-1, 353-2: side plate for solution drip tray
373-1, 373-2: side plate for aerosol prevention part
471: aerosol prevention tube supporting plate
471-H: through-hole 473: aerosol prevention tube
571: aerosol prevention tube supporting plate
571-H: through-hole
573: aerosol prevention tube 575: aerosol prevention container
671: aerosol prevention block 671-H: through-hole
771: upper plate for aerosol prevention part
771-H: through-hole 775: aerosol prevention container
1050: solution drip tray 1070: aerosol prevention part
P: pipette Mode for the Invention Hereinafter, the embodiments of the present invention will be described in detail with reference to accompanying drawings.

First Embodiment

A first embodiment relates to an automatic purification apparatus for isolating target nucleic acids from a plurality of biological samples.

Figure 2:
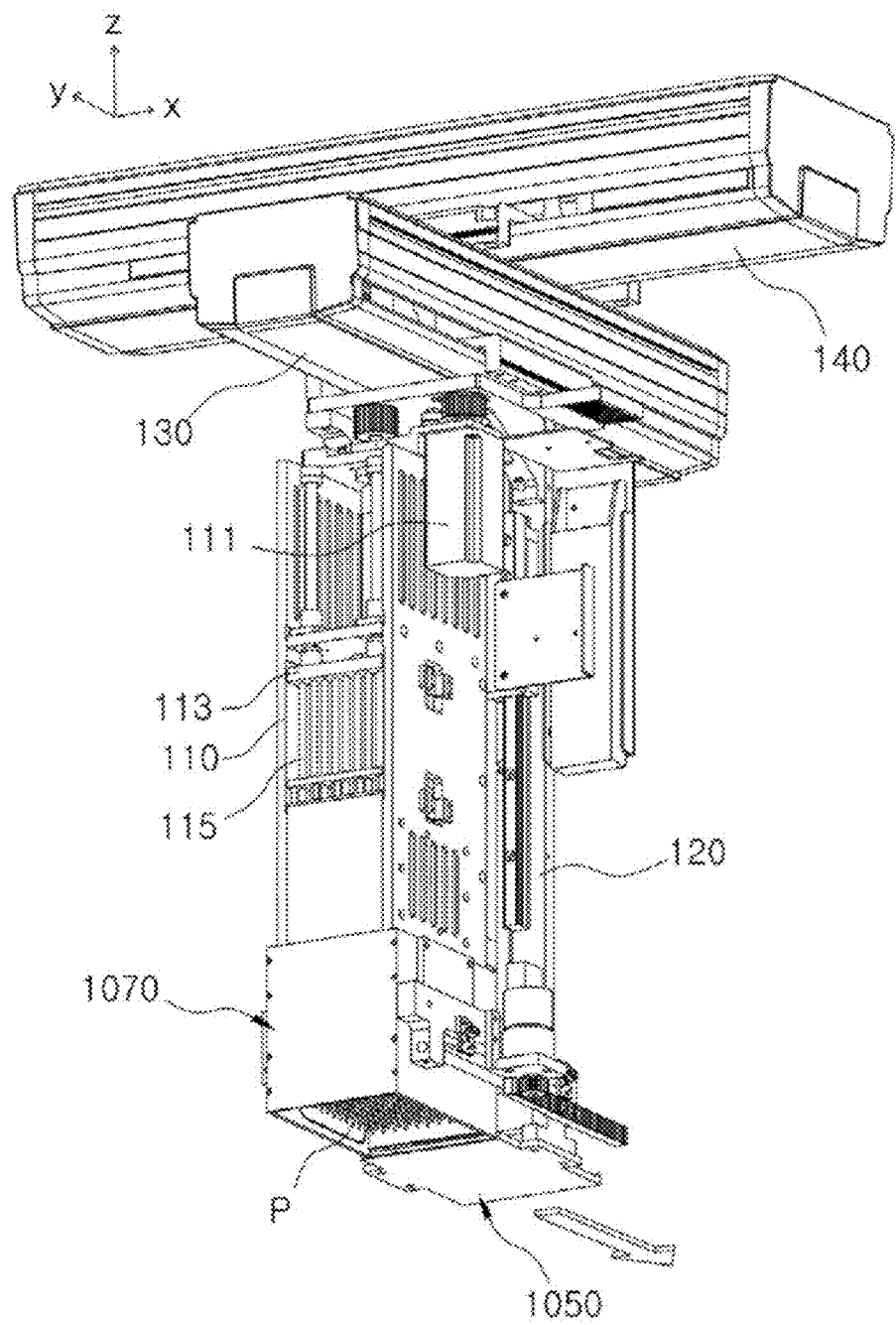
Figure 3:
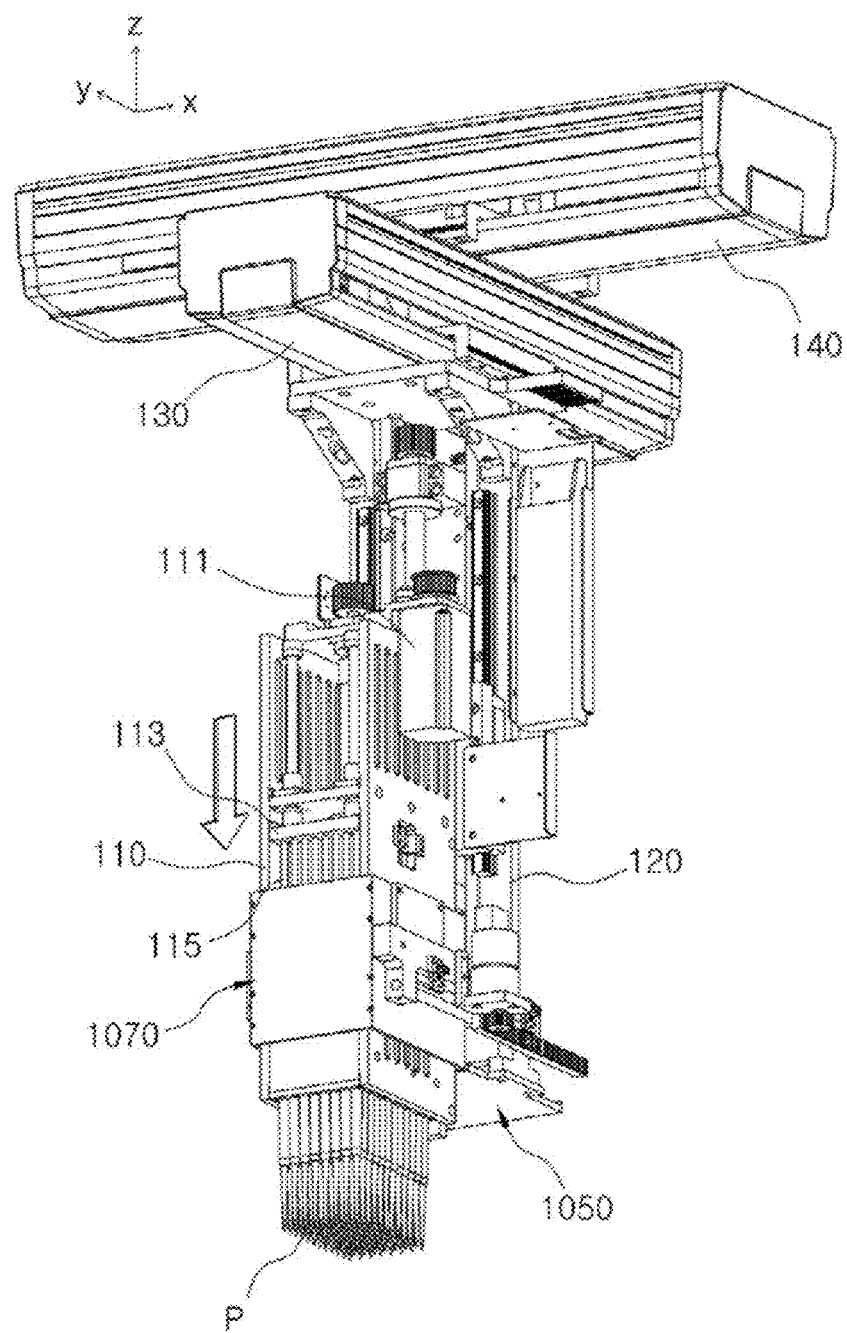
Figure 4:
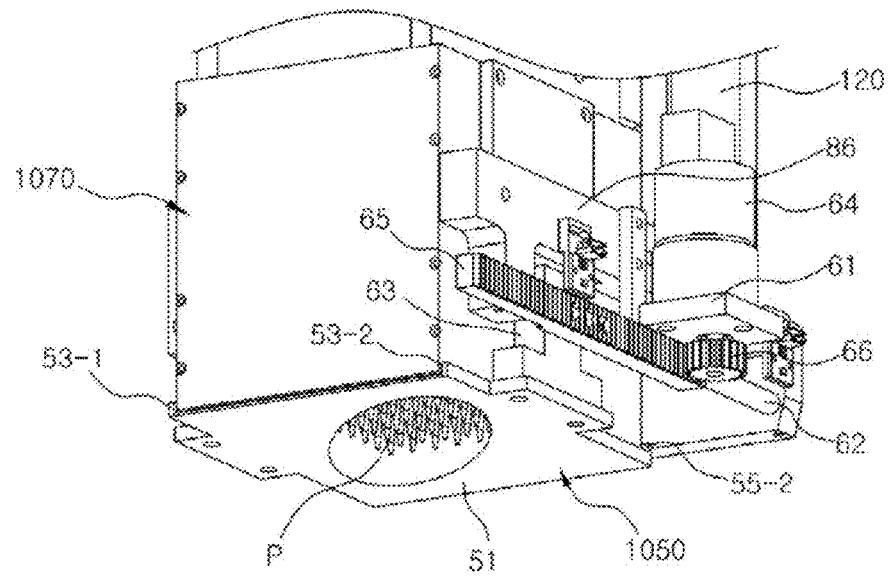
FIGS. 4 and 5 are perspective views of main parts of FIGS. 1 and 2.
Figure 5:
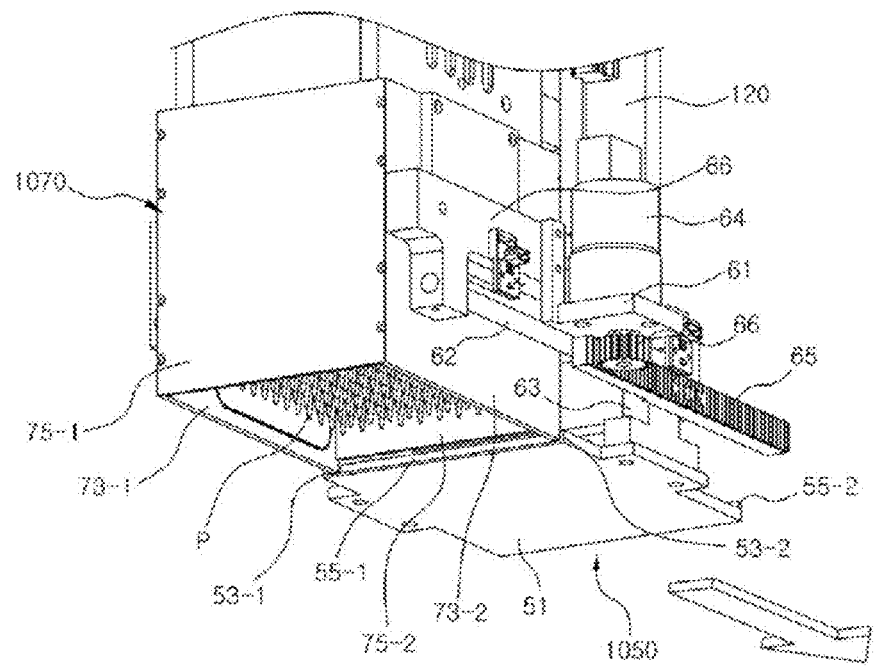

FIGS. 1, 2 and 3 are perspective views showing a first embodiment of the present invention, and FIGS. 4 and 5 are perspective views of main parts of FIGS. 1 and 2.

Referring to FIGS. 1 to 3, the first embodiment includes a purification block 110 for isolating target nucleic acids from a plurality of biological samples. The purification block 110 is disposed at a purification block supporting part 120 so as to be slid up and down.

Although not shown in FIGS. 1 to 3, a purification block lifting motor 151 (referring to FIG. 7) is installed at the purification block supporting part 120 so as to move the purification block 110 up and down.

Referring to FIGS. 1 to 3, the purification block supporting part 120 is disposed at a first horizontal guider 130 so as to be horizontally slid in a y-axial direction. The first horizontal guider 130 is disposed at a second horizontal guider 140 so as to be horizontally slid in an x-axial direction. The x-axial direction is orthogonal to the y-axial direction. A moving means for moving the purification block supporting part 120 and the first horizontal guider 130 in the x-axial direction and the y-axial direction is not shown in the drawings.

Referring to FIGS. 1 to 3, a syringe pin holder 113 is installed at the purification block 110 so as to be slide up and down. A plurality of syringe pins 115 are fixed to the syringe pin holder 113. Meanwhile, a syringe pin moving motor 111 for moving the syringe pin holder 113 up and down is fixed to the purification block 110.

Referring to FIGS. 1 to 3, a plurality of pipettes P or a plurality of magnet rod tubes (not shown) are installed at a lower end of the purification block 110.

Referring to FIGS. 1 to 5, the first embodiment includes a solution drip tray 1050. The solution drip tray 1050 is disposed so as to be spaced apart from lower ends of the plurality of pipettes P or the plurality of magnet rod tubes (not shown) and also to be movable to a position where the solution drip tray 1050 can receive solution drips from the plurality of pipettes P or the plurality of magnet rod tubes (not shown). Further, the solution drip tray 1050 is also movable to another position where the solution drip tray 1050 can avoid in contact with plurality of pipettes P or the plurality of magnet rod tubes (not shown) when the purification block 110 is moved down. A solution drip tray moving means for moving the solution drip tray 1050 between the above-mentioned positions will be described later.

Referring to FIG. 5, the solution drip tray 1050 is provided with a lower plate 51 for solution drip tray. The lower plate 51 for solution drip tray has a sufficient surface area in order to receive all of the solution drips from the plurality of pipettes P or the plurality of magnet rod tubes (not shown).

Referring to FIG. 5, first, second, third and fourth tightly-contacting plates 53-1, 55-1, 53-2 and 55-2 for solution drip tray are vertically formed at edge portions of an upper surface of the lower plate 51 for solution drip tray.

Referring to FIGS. 4 and 5, an inner side surface of the first tightly-contacting plate 53-1 for solution drip tray is formed to be tightly contacted with an outer surface of a first side plate 73-1 for aerosol preventing part, and an outer side surface of the second tightly-contacting plate 55-1 for solution drip tray is formed to be tightly contacted with an inner surface of a second side plate 75-1 for aerosol preventing part. And an inner side surface of the third tightly-contacting plate 53-2 for solution drip tray is formed to be tightly contacted with an outer surface of a third side plate 73-2 for aerosol preventing part, and an inner side surface of the fourth tightly-contacting plate 55-2 for solution drip tray is formed to be tightly contacted with an outer surface of a fourth side plate 75-2 for aerosol preventing part.

Referring to FIGS. 1 to 5, the first embodiment includes a box-shaped aerosol prevention part 1070 which is fixedly installed at a certain vertical position so that an upper inner surface thereof is tightly contacted with an outer surface of the purification block 110 and a lower end thereof is tightly contacted with the solution drip tray 1050, when the purification block 110 is moved upward. The aerosol prevention part 1070 is tightly contacted with the solution drip tray 1050 which is located at the position where the solution drip tray 1050 can receive the solution drips, so that the portions of the plurality of pipettes P or the plurality of magnet rod tubes, which are smeared with a solution containing the target nucleic acid, are shut off from the outside. Since the aerosol prevention part 1070 is tightly contacted with the solution drip tray 1050 and thus the portions of the plurality of pipettes P or the plurality of magnet rod tubes, which are smeared with a solution containing the target nucleic acid, are shut off from the outside, an air flow passing through among the plurality of pipettes P or the plurality of magnet rod tubes is not generated when the purification block 110 is moved horizontally. Therefore, it is prevented that the aerosol is generated from the solution containing the target nucleic acid, which is smeared on the circumferential surface of one of the plurality of pipettes P or the plurality of magnet rod tubes, when the purification block 110 is moved horizontally, and then attached to the circumferential surfaces of another pipettes P or another magnet rod tubes.

Referring to FIGS. 4 and 5, the aerosol prevention part 1070 includes a first side plate 73-1 for aerosol prevention part, a second side plate 75-1 for aerosol prevention part, a third side plate 73-2 for aerosol prevention part and a fourth side plate 75-2 for aerosol prevention part. The aerosol prevention part 1070 is generally is formed into a rectangular box shape.

Referring to FIGS. 4 and 5, a fixed block 86 for aerosol prevention part is fixed to the purification block supporting part 120. Since the third side plate 73-2 for aerosol prevention part is fixed to the fixed block 86 for aerosol prevention part, the aerosol prevention part 1070 is fixedly installed at the certain vertical position. Meanwhile, the first side plate 73-1 for aerosol prevention part is disposed to be faced with the third side plate 73-2 for aerosol prevention part, and the second side plate 75-1 for aerosol prevention part is disposed to be faced with the fourth side plate 75-2 for aerosol prevention part. A lower end of the fourth side plate 75-2 for aerosol prevention part is located at higher position than a lower end of the second side plate 75-1 for aerosol prevention part. Meanwhile an outer surface of the first side plate 73-1 for aerosol prevention part is tightly contacted with an inner surface of the first tightly-contacting plates 53-1 for solution drip tray, and an inner surface of the second side plate 75-1 for aerosol prevention part is tightly contacted with an outer surface of the second tightly-contacting plates 55-1 for solution drip tray, and an outer surface of the third side plate 73-2 for aerosol prevention part is tightly contacted with an inner surface of the third tightly-contacting plates 53-2 for solution drip tray, and an outer surface of the fourth side plate 75-2 for aerosol prevention part is tightly contacted with an inner surface of the fourth tightly-contacting plates 55-2 for solution drip tray. Therefore, airtightness between the solution drip tray 1050 and the aerosol prevention part 1070 is enhanced.

Hereinafter, the solution drip tray moving means will be described.

Referring to FIGS. 4 and 5, a solution drip tray supporting part 61 is connected to the fixed block 86 for aerosol prevention part.

Referring to FIGS. 4 and 5, a guiding rod 62 for solution drip tray is disposed between the fixed block 86 for aerosol prevention part and the purification block supporting part 120. A solution drip tray slider 63 is installed at the guiding rod 62 for solution drip tray so as to be horizontally moved along the guiding rod 62 for solution drip tray.

Referring to FIGS. 4 and 5, a solution drip tray moving motor 64 is fixed to the solution drip tray supporting part 61, and a pinion 66 is rotatably connected to the solution drip tray moving motor 64. Meanwhile, a rack 65 which is engaged with the pinion 66 is fixed to the solution drip tray slider 63. Therefore, if the pinion is rotated by the solution drip tray moving motor 64, the solution drip tray slider 63 is horizontally moved along the guiding rod 62.

Referring to FIGS. 4 and 5, the lower plate 51 for solution drip tray is fixedly connected to the solution drip tray slider 63. Therefore, when the solution drip tray slider 63 is horizontally moved, the solution drip try 1050 is also moved horizontally. Meanwhile, the solution drip tray 1050 is disposed so that the lower plate 51 for solution drip tray can be moved along the same horizontal plane when the solution drip tray slider 63 is moved. Since the lower plate 51 for solution drip tray is moved along the same horizontal plane, the air flow generated by the movement of the lower plate 51 for solution drip tray is minimized.

Second Embodiment

A second embodiment relates to another automatic purification apparatus for isolating target nucleic acids from a plurality of biological samples.

Figure 6:
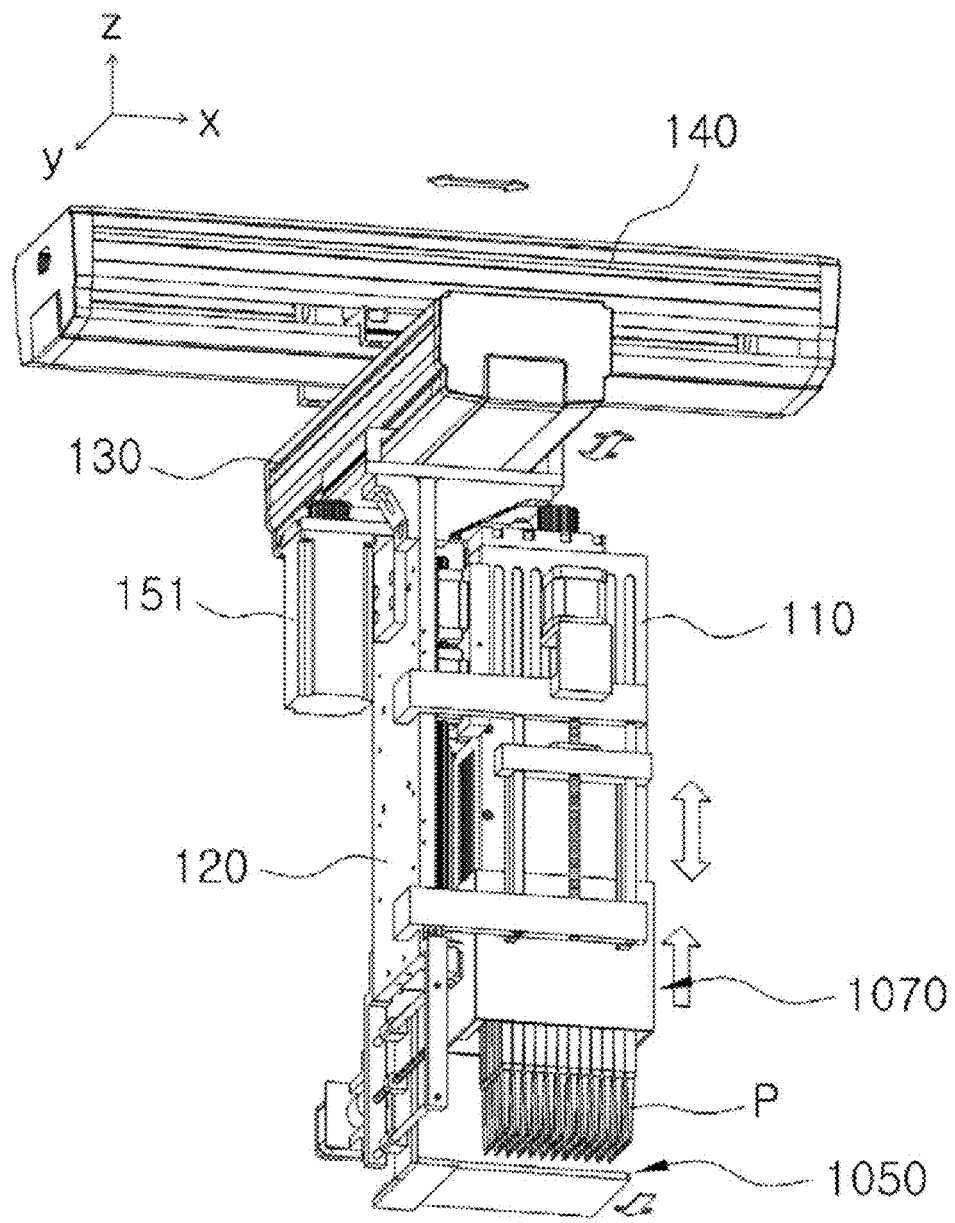
FIGS. 6 and 7 are perspective views showing a second embodiment of the present invention.
Figure 7:
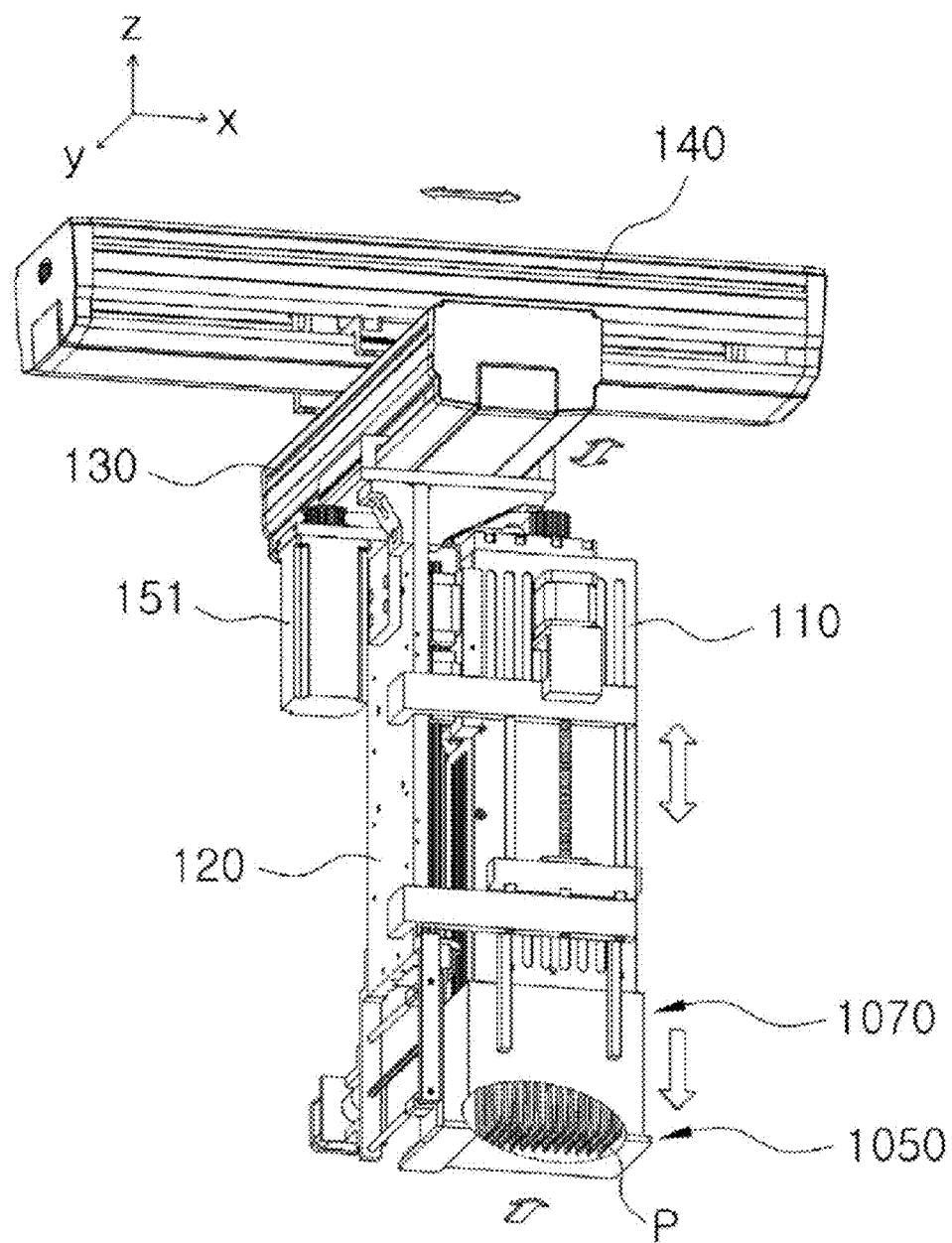
Figure 8:
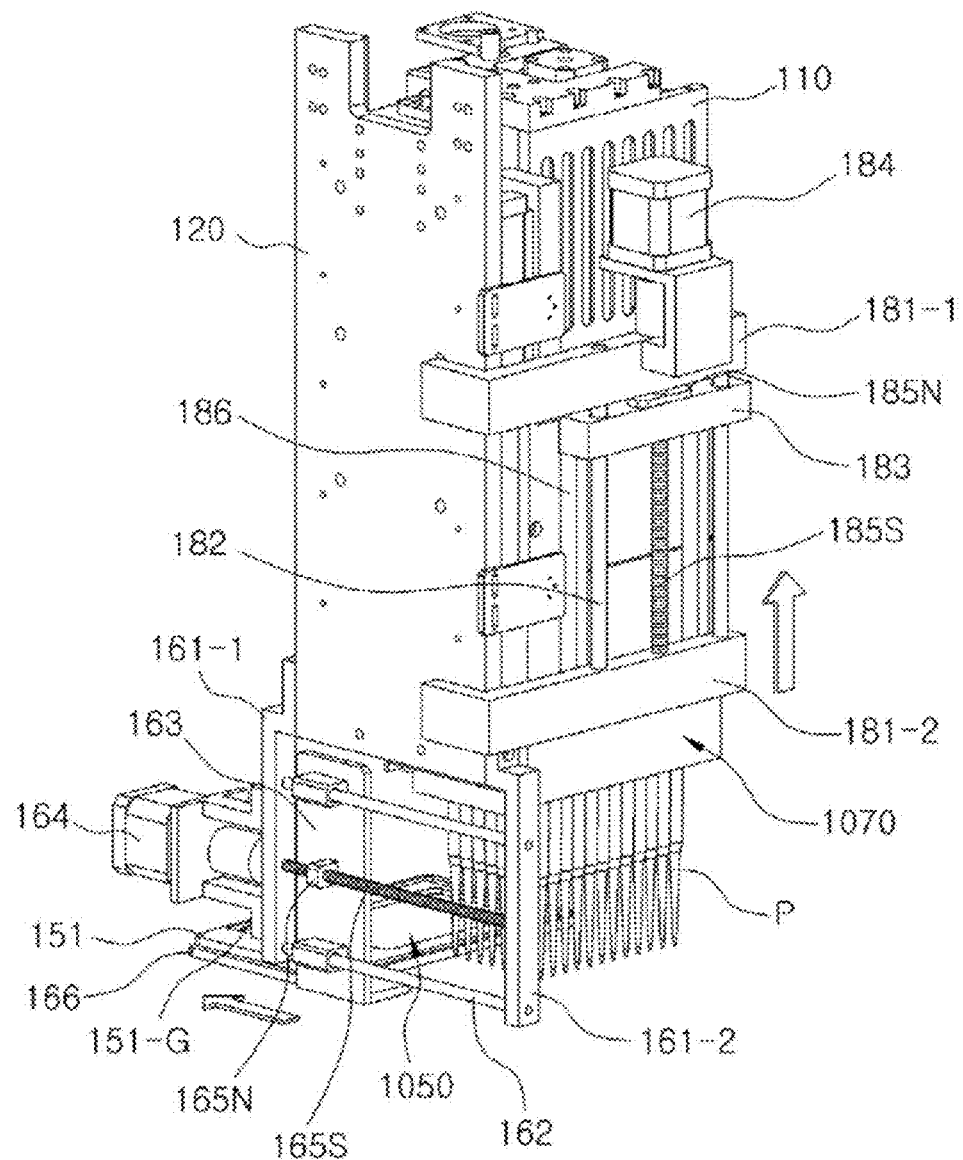
FIGS. 8 and 9 are perspective views of main parts of the second embodiment of the present invention.
Figure 9:
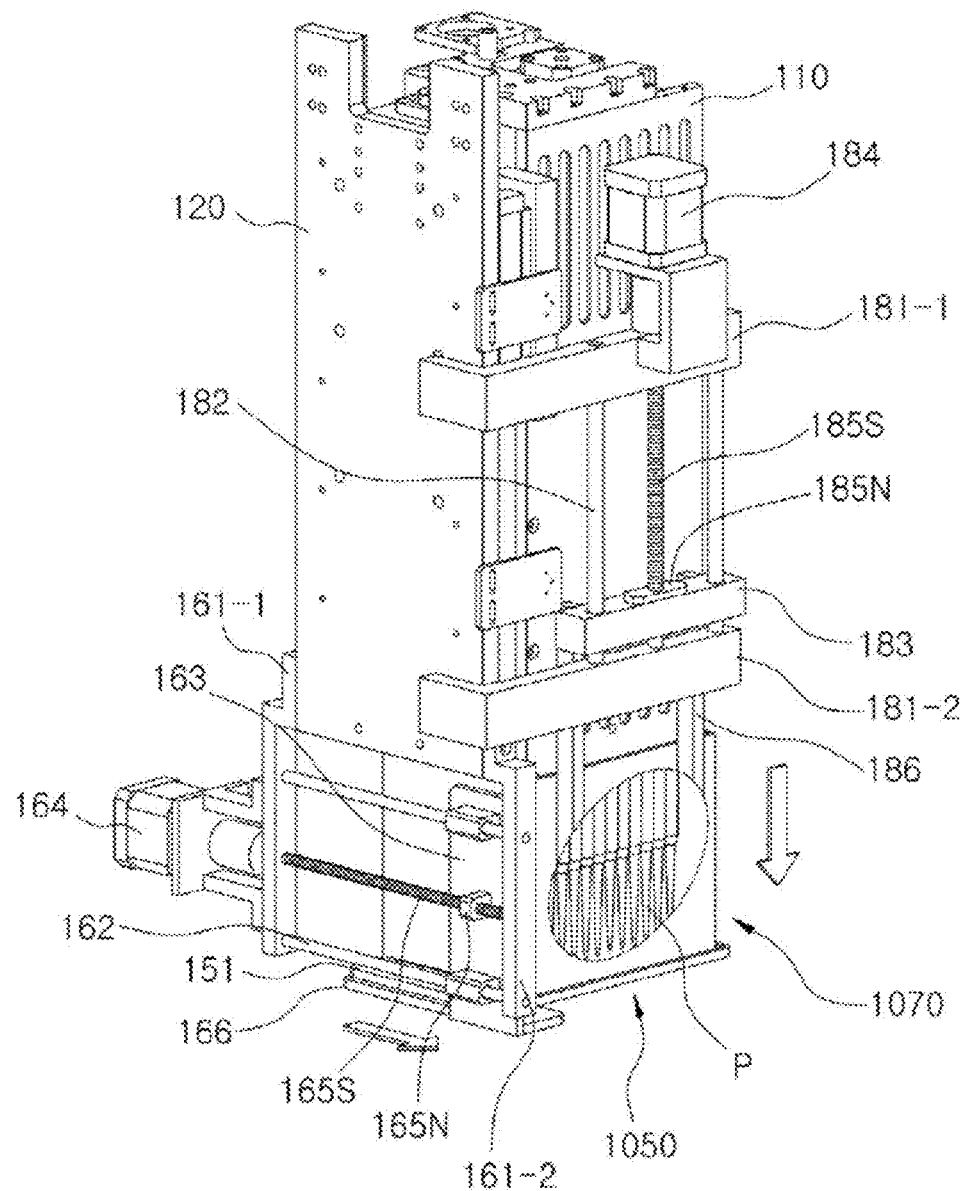

FIGS. 6 and 7 are perspective views showing a second embodiment of the present invention, and FIGS. 8 and 9 are perspective views of main parts of the second embodiment of the present invention.

Referring to FIGS. 6 and 7, the second embodiment includes a purification block 110 for isolating target nucleic acids from a plurality of biological samples. The purification block 110 is disposed at a purification block supporting part 120 so as to be slid up and down.

Referring to FIGS. 6 and 7, a purification block lifting motor 151 is installed at the purification block supporting part 120 so as to move the purification block 110 up and down.

Referring to FIGS. 6 and 7, the purification block supporting part 120 is disposed at a first horizontal guider 130 so as to be horizontally slid in a y-axial direction. The first horizontal guider 130 is disposed at a second horizontal guider 140 so as to be horizontally slid in an x-axial direction. The x-axial direction is orthogonal to the y-axial direction. A moving means for moving the purification block supporting part 120 and the first horizontal guider 130 in the x-axial direction and the y-axial direction is not shown in the drawings.

Referring to FIGS. 6 and 7, a plurality of pipettes P or a plurality of magnet rod tube (not shown) are installed at a lower end of the purification block 110.

Referring to FIGS. 6 to 9, the second embodiment includes a solution drip tray 1050. The solution drip tray 1050 is disposed so as to be spaced apart from a lower end of the plurality of pipettes P or the plurality of magnet rod tubes (not shown) and also to be movable to a position where the solution drip tray 1050 can receive solution drips from the plurality of pipettes P or the plurality of magnet rod tubes (not shown). Further, the solution drip tray 1050 is also movable to another position where the solution drip tray 1050 can avoid in contact with plurality of pipettes P or the plurality of magnet rod tubes (not shown) when the purification block 110 is moved down. A solution drip tray moving means for moving the solution drip tray 1050 between the above-mentioned positions will be described later.

Referring to FIG. 8, the solution drip tray 1050 is provided with a lower plate 151 for solution drip tray. The lower plate 151 for solution drip tray has a sufficient surface area in order to receive all of the solution drips from the plurality of pipettes P or the plurality of magnet rod tubes (not shown). An insertion groove 151-G formed into a looped curve is formed in an upper surface of the lower plate 151 for solution drip tray.

Referring to FIGS. 6 and 7, the second embodiment includes an aerosol prevention part 1070 which is disposed so as to be moved to up and down directions of the purification block 110. The aerosol prevention part 1070 is moved in the down direction of the purification block 110 so as to be tightly contacted with the solution drip tray 1050 which is located at the position where the solution drip tray 1050 can receive the solution drips, so that the portions of the plurality of pipettes P or the plurality of magnet rod tubes, which are smeared with a solution containing the target nucleic acid, are shut off from the outside. Since the aerosol prevention part 1070 is tightly contacted with the solution drip tray 1050 and thus the portions of the plurality of pipettes P or the plurality of magnet rod tubes, which are smeared with a solution containing the target nucleic acid, are shut off from the outside, an air flow passing through among the plurality of pipettes P or the plurality of magnet rod tubes is not generated when the purification block 110 is moved horizontally. Therefore, it is prevented that the aerosol is generated from the solution containing the target nucleic acid, which is smeared on the circumferential surface of one of the plurality of pipettes P or the plurality of magnet rod tubes, when the purification block 110 is moved horizontally, and then attached to the circumferential surfaces of another pipettes P or another magnet rod tubes. An aerosol prevention part moving means for moving the aerosol prevention part 1070 in the up and down direction of the purification block 110 will be described later.

Referring to FIGS. 6 and 8, the aerosol prevention part 1070 is formed into a box shape of which an upper inner surface is tightly contacted with the outer surface of the purification block 110 and a lower end is tightly contacted with an upper surface of the solution drip tray 1050 when the aerosol prevention part 1070 is moved down. In other words, the aerosol prevention part 1070 is formed into the box shape so as be movable up and down while enclosing the outer surface of the purification block 110. Meanwhile, the lower end of the aerosol prevention part 1070 is formed to be inserted into the insertion groove 151-G of the solution drip tray 1050. Since the lower end of the aerosol prevention part 1070 is inserted into the insertion groove 151-G of the solution drip tray 1050, airtightness between the solution drip tray 1050 and the aerosol prevention part 1070 is enhanced.

Hereinafter, the solution drip tray moving means will be described.

Referring to FIGS. 8 and 9, two first supporting parts 161-1 and 161-2 for solution drip tray are connected to a lower end of the purification block supporting part 120 so as to be spaced apart from each other.

Referring to FIGS. 8 and 9, a guiding rod 162 for solution drip tray is disposed between the first supporting parts 161-1 and 161-2 for solution drip tray. A solution drip tray slider (not designated by a reference numeral) is installed at the guiding rod 162 for solution drip tray so as to be horizontally moved along the guiding rod 162 for solution drip tray.

Referring to FIGS. 8 and 9, the solution drip tray slider (not designated by a reference numeral) is fixed to a moving plate 163 for solution drip tray, which is disposed between the first supporting parts 161-1 and 161-2 for solution drip tray.

Referring to FIGS. 8 and 9, a solution drip tray moving motor 164 is fixed to the first supporting part 161-1 for solution drip tray, and a ball screw 165S for solution drip tray is rotatably connected to the solution drip tray moving motor 164. The ball screw 165S for solution drip tray is rotatably supported by the first supporting parts 161-1 and 161-2 for solution drip tray.

Referring to FIGS. 8 and 9, a ball nut 165N for solution drip tray is inserted onto the ball screw 165S for solution drip tray. The ball nut 165N for solution drip tray is formed with a female thread corresponding to a male thread of the ball screw 165S for solution drip tray. Meanwhile, the ball nut 165N for solution drip tray is fixed to the moving plate 163 for solution drip tray. Therefore, if the ball screw 165S for solution drip tray is rotated by the solution drip tray moving motor 164, the moving plate 163 for solution drip tray is horizontally moved along the guiding rod 162 for solution drip tray.

Referring to FIGS. 8 and 9, a second supporting part 166 for solution drip tray is fixed to the moving plate 163 for solution drip tray, and the solution drip tray 1050 is fixed to an upper surface of the second supporting part 166 for solution drip tray. Therefore, as the moving plate 163 for solution drip tray is horizontally moved, the solution drip tray 1050 is also moved horizontally. Meanwhile, the solution drip tray 1050 is installed so that the lower plate 151 for solution drip tray is moved along the same horizontal plane when the moving plate 163 for solution drip tray is moved. Since the lower plate 151 for solution drip tray is moved along the same horizontal plane, the air flow generated by the movement of the lower plate 151 for solution drip tray is minimized.

Hereinafter, the aerosol prevention part moving means will be described.

Referring to FIGS. 8 and 9, two first supporting parts 181-1 and 181-2 for aerosol prevention part are connected to a side surface of the purification block supporting part 120 so as to be spaced apart from each other in up and down directions.

Referring to FIGS. 8 and 9, a guiding rod 182 for aerosol prevention part is disposed between the first supporting parts 181-1 and 181-2 for aerosol prevention part. A moving block 183 for aerosol prevention part is installed at the guiding rod 182 for aerosol prevention part so as to be moved up and down along the guiding rod 182 for aerosol prevention part.

Referring to FIGS. 8 and 9, a aerosol prevention part moving motor 184 is fixed to the first supporting part 181-1 for aerosol prevention part, and a ball screw 185S for aerosol prevention part is rotatably connected to the aerosol prevention part moving motor 184. The ball screw 185S for aerosol prevention part is rotatably supported by the first supporting parts 181-1 and 181-2 for aerosol prevention part.

Referring to FIGS. 8 and 9, a ball nut 185N for aerosol prevention part is inserted onto the ball screw 185S for aerosol prevention part. The ball nut 185N for aerosol prevention part is formed with a female thread corresponding to a male thread of the ball screw 185S for aerosol prevention part. Meanwhile, the ball nut 185N for aerosol prevention part is fixed to the moving block 183 for aerosol prevention part. Therefore, if the ball screw 185S for aerosol prevention part is rotated by the aerosol prevention part moving motor 184, the moving block 183 for aerosol prevention part is moved up and down along the guiding rod 182 for aerosol prevention part.

Referring to FIGS. 8 and 9, an upper end of a second supporting part 186 for aerosol prevention part is fixed to the moving block 183 for aerosol prevention part, and the aerosol prevention part 1070 is fixed to a lower end of the second supporting part 186 for aerosol prevention part. Therefore, as the moving block 183 for aerosol prevention part is moved down, the aerosol prevention part 1070 is also moved down. Meanwhile, the aerosol prevention part 1070 is installed so that respective four side plates for aerosol prevention part of the aerosol prevention part 1070 are moved along the same vertical surfaces when the moving block 183 for aerosol prevention part is moved. Since the respective four side plates for aerosol prevent part are moved along the same vertical surfaces, the air flow generated by the movement of the four side plates for aerosol prevent part is minimized.

Third Embodiment

A third embodiment relates to yet another automatic purification apparatus for isolating target nucleic acids from a plurality of biological samples.

Figure 10:
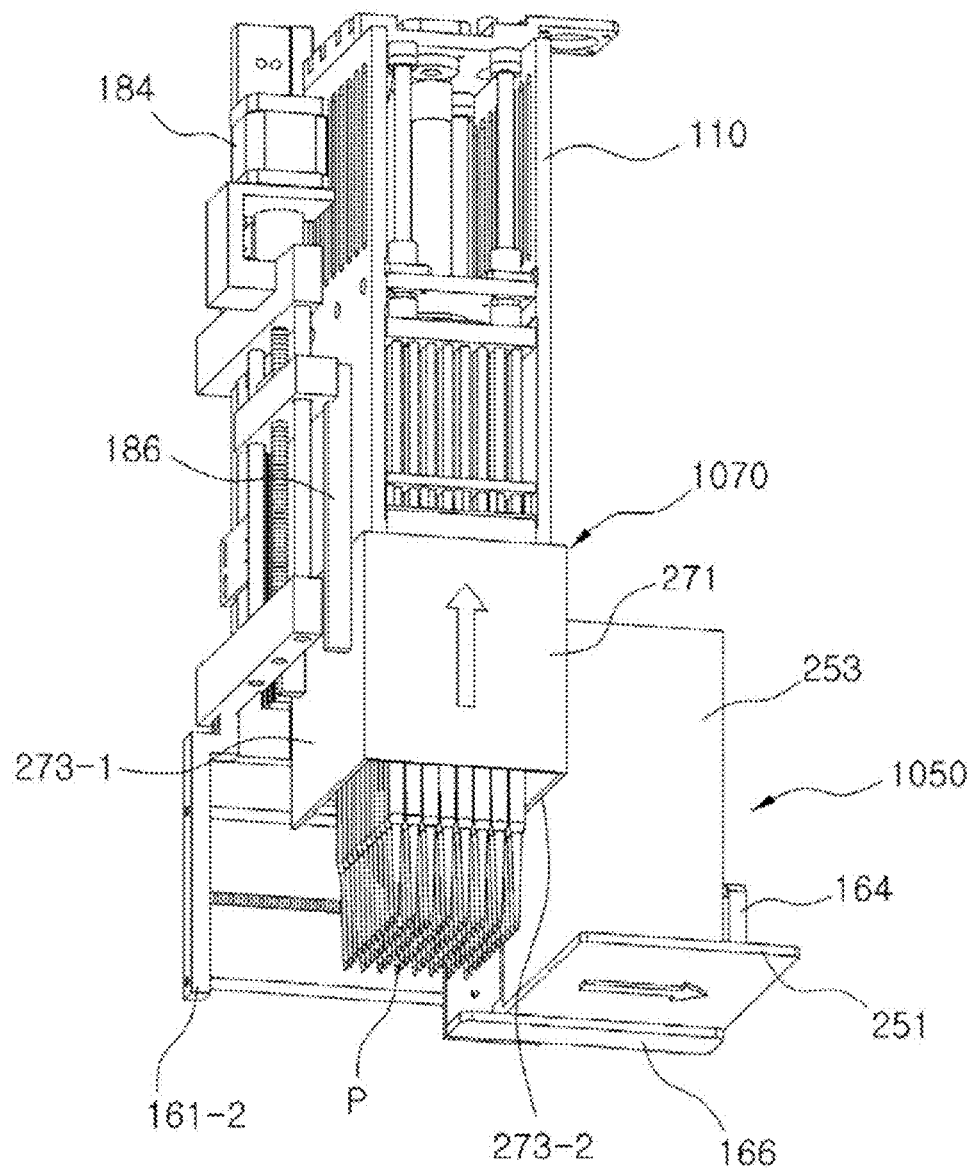
FIGS. 10 and 11 are perspective views of main parts of a third embodiment of the present invention.
Figure 11:
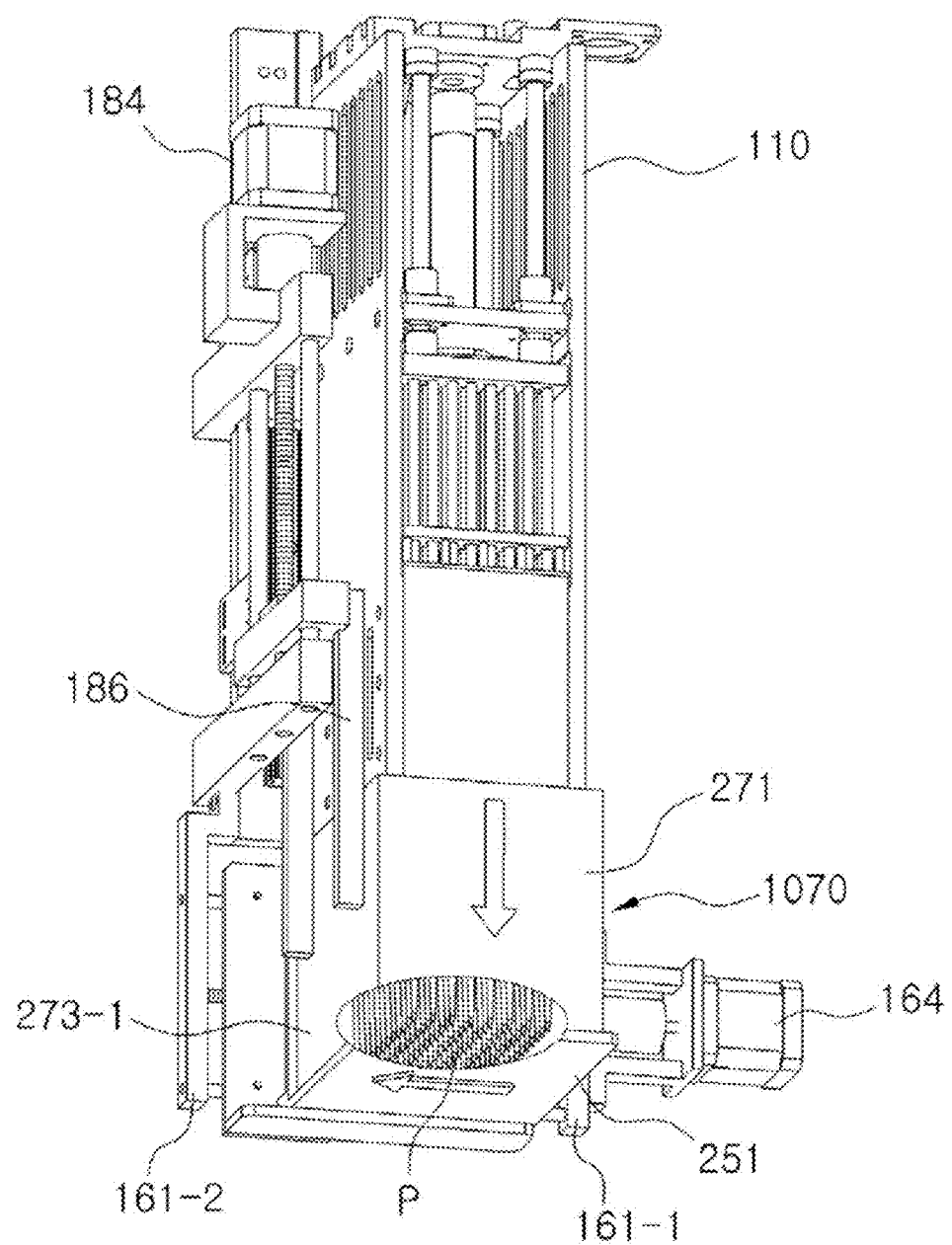

FIGS. 10 and 11 are perspective views of main parts of a third embodiment of the present invention.

The third embodiment is the same as the second embodiment except the solution drip tray 1050 and the aerosol prevention part 1070. Therefore, the same reference numerals and technical terms are used for the same elements.

Referring to FIG. 10, the solution drip tray 1050 has a lower plate 251 for solution drip tray and a side plate 253 for solution drip tray.

Referring to FIGS. 10 and 11, the lower plate 251 for solution drip tray is disposed horizontally. The lower plate 251 for solution drip tray is fixed to the second supporting part 166 for solution drip tray. The lower plate 251 for solution drip tray is disposed to be moved along the same horizontal plane when the second supporting part 166 for solution drip tray is moved. Therefore, the air flow generated by the movement of the lower plate 251 for solution drip tray is minimized. Like in the second embodiment, the lower plate 251 for solution drip tray has a sufficient surface area in order to receive all of the solution drips from the plurality of pipettes P or the plurality of magnet rod tubes (not shown). Meanwhile, although not shown in the drawings, edge portion of an upper surface of the lower plate 251 for solution drip tray is formed with an insertion groove (not shown) in which a lower end of the aerosol prevention part 1070 is inserted.

Referring to FIGS. 10 and 11, the side plate 253 for solution drip tray is uprightly disposed at an edge portion of the lower plate 251 for solution drip tray. The side plate 253 for solution drip tray is disposed to be moved along the same vertical surface when the second supporting part 166 for solution drip tray is moved, and thus the air flow generated by the movement of the side plate 253 for solution drip tray is minimized. Accordingly, the solution drip tray 1050 has an longitudinally "L"-shaped cross section. The side plate 253 for solution drip tray is disposed so that an upper end thereof is tightly contacted with a side surface of the purification block 110 when the solution drip tray 1050 is moved.

Referring to FIG. 10, the aerosol prevention part 1070 has three side plates 271, 273-1 and 273-2 for aerosol prevention part. The three side plates 271, 273-1 and 273-2 for aerosol prevention part are connected with each other so as to provide an transversely "U"-shaped cross section. The side plate 273-1 for aerosol prevention part is fixedly connected to a lower portion of the second supporting part 186 for aerosol prevention part. Meanwhile, the aerosol prevention part 1070 is disposed so that the three side plates 271, 273-1 and 273-2 for aerosol prevention part are respectively moved along the same vertical surfaces when the aerosol prevention part 1070 is moved down. Since the three side plates 271, 273-1 and 273-2 for aerosol prevention part are respectively moved along the same vertical surfaces, the air flow generated by the movement of the three side plates 271, 273-1 and 273-2 for aerosol prevention part is minimized.

Referring to FIG. 11, the aerosol prevention part 1070 is installed so that an upper inner surface thereof is tightly contacted with the outer surface of the purification block 110 and a lower end thereof is inserted into the insertion groove (not shown) of the lower plate 251 for solution drip tray when the aerosol prevention part 1070 is moved down. Further, the aerosol prevention part 1070 is also installed so that both side ends of opened circumferential surface thereof, i.e., exposed side ends of the two side plates 273-1 and 273-2 for aerosol prevention part are tightly contacted with the side plate 253 for solution drip tray when the aerosol prevention part 1070 is moved down.

Fourth Embodiment

A fourth embodiment relates to yet another automatic purification apparatus for isolating target nucleic acids from a plurality of biological samples.

Referring to FIGS. 10 and 11, a solution drip tray and an aerosol prevention part of the fourth embodiment have the same structure as those of third embodiment. Therefore, the same reference numerals and technical terms are used for the same elements. In the fourth embodiment, the aerosol prevention part 1070 is fixedly installed at a vertical position in which an upper inner surface thereof can be tightly contacted with the outer surface of the purification block 110 when the purification block 110 is moved upward. Therefore, the fourth embodiment does not include the aerosol prevention part moving means for moving up and down the aerosol prevention part 1070. Further, unlike in the third embodiment, the lower plate 251 for solution drip tray is not formed with the insertion groove (not shown) in which the lower end of the aerosol prevention part 1070 is inserted. Thus, the lower plate 251 for solution drip tray of the fourth embodiment may be formed with a tightly-contacting plate equivalent to the tightly-contacting plates 53-1, 53-2, 55-1 and 55-2 for solution drip tray (referring to FIG. 5) of the first embodiment. The other matters are the same as in the third embodiment.

Fifth Embodiment

A fifth embodiment relates to yet another automatic purification apparatus for isolating target nucleic acids from a plurality of biological samples.

Figure 12:
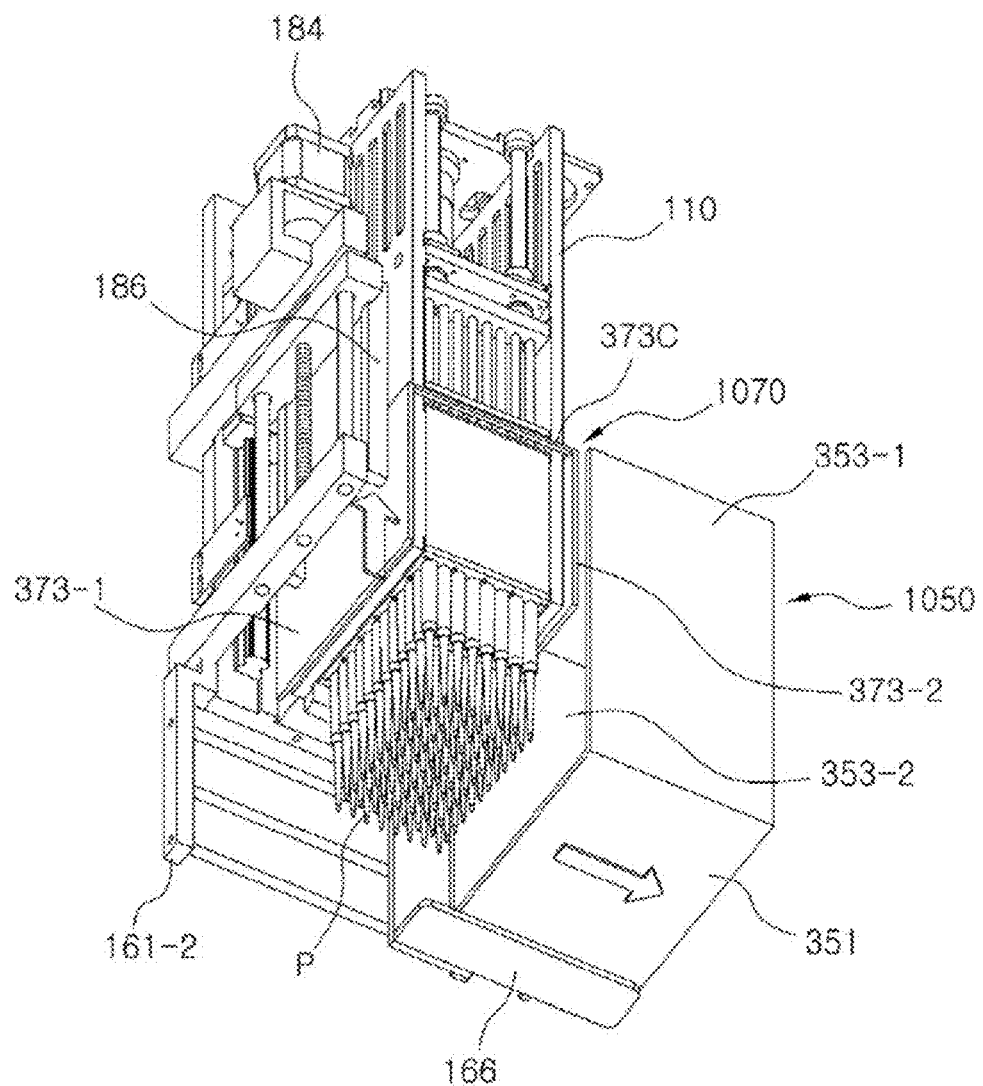
FIGS. 12 and 13 are perspective views of main parts of a fourth embodiment of the present invention.
Figure 13:
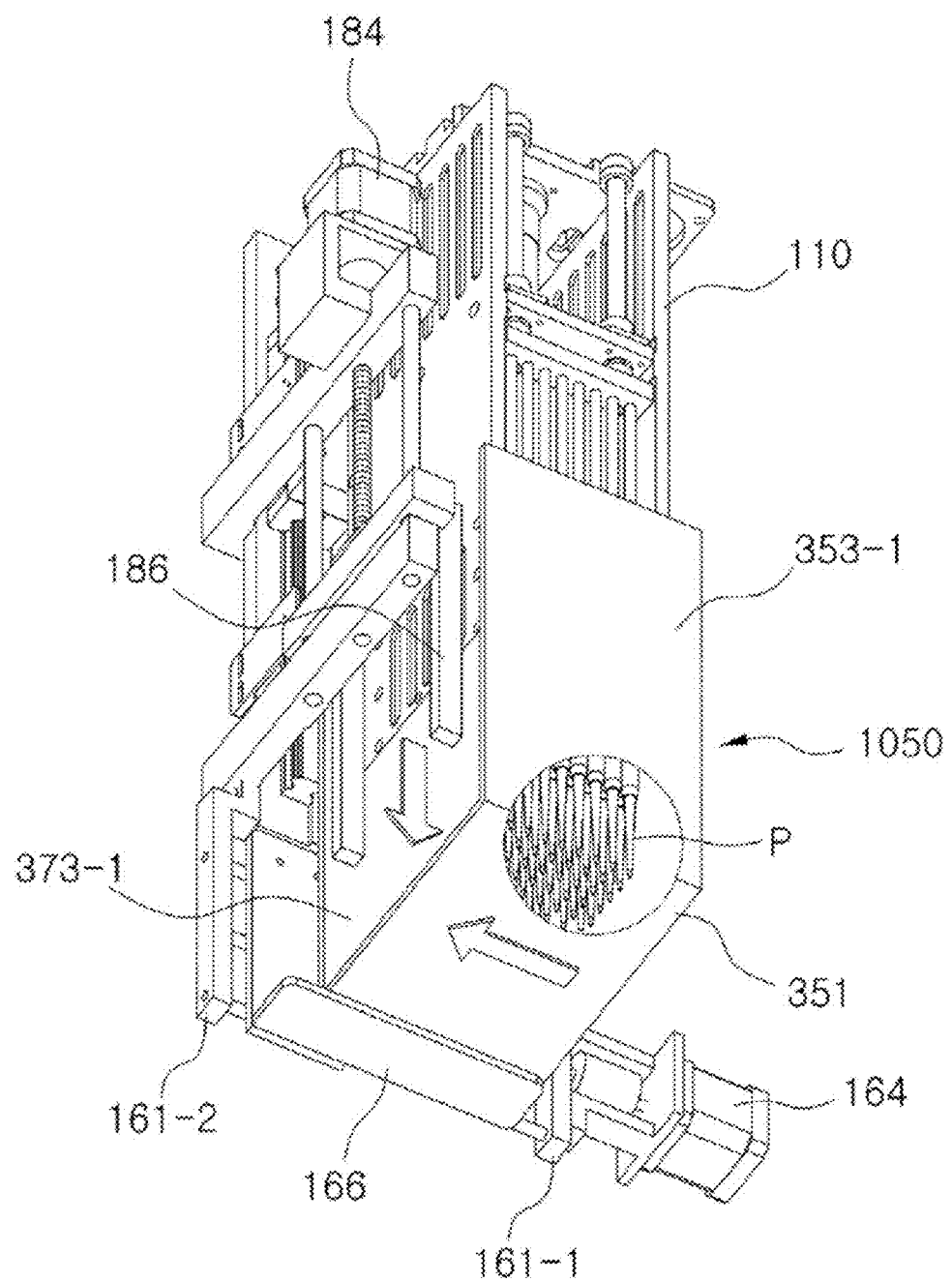

FIGS. 12 and 13 are perspective views of main parts of a fourth embodiment of the present invention.

The fifth embodiment is the same as the second embodiment except the solution drip tray 1050 and the aerosol prevention part 1070. Therefore, the same reference numerals and technical terms are used for the same elements.

Referring to FIG. 12, the solution drip tray 1050 has a lower plate 351 for solution drip tray and two side plates 353-1 and 353-2 for solution drip tray.

Referring to FIGS. 12 and 13, the lower plate 351 for solution drip tray is disposed horizontally. The lower plate 351 for solution drip tray is fixed to the second supporting part 166 for solution drip tray. The lower plate 351 for solution drip tray is disposed so as to be moved along the same horizontal plane when the second supporting part 166 for solution drip tray is moved. Therefore, the air flow generated by the movement of the lower plate 351 for solution drip tray is minimized. Like in the second embodiment, the lower plate 351 for solution drip tray has a sufficient surface area in order to receive all of the solution drips from the plurality of pipettes P or the plurality of magnet rod tubes (not shown). Meanwhile, although not shown in the drawings, the lower plate 351 for solution drip tray is formed with two insertion grooves (not shown) which are straightly arranged to be spaced apart from each other and in which lower ends of two side plates 353-1 and 353-2 for solution drip tray are inserted so as to enhance the air-tightness.

Referring to FIGS. 12 and 13, the two side plates 353-1 and 353-2 for solution drip tray are uprightly disposed at edge portions of the lower plate 351 for solution drip tray. The two side plate 353 for solution drip tray are disposed to be moved along the same vertical surfaces when the second supporting part 166 for solution drip tray is moved, and thus the air flow generated by the movement of the two side plates 353-1 and 353-2 for solution drip tray is minimized. Accordingly, the solution drip tray 1050 has a longitudinally "U"-shaped cross section. The two side plates 353-1 and 353-2 for solution drip tray are disposed so that upper ends thereof are tightly contacted with side surfaces of the purification block 110 when the solution drip tray 1050 is moved.

Referring to FIG. 12, the aerosol prevention part 1070 has two side plates 373-1 and 373-2 for aerosol prevention part. Upper ends of the two side plates 373-1 and 373-2 for aerosol prevention part are connected with each other through a side-plate connection part 373C so that the two side plates 373-1 and 373-2 for aerosol prevention part are parallelly faced with each other and the purification block 110 is interposed therebetween.

Referring to FIGS. 12 and 13, the side plate 373-1 for aerosol prevention part is fixedly connected to a lower portion of the second supporting part 186 for aerosol prevention part. Meanwhile, the aerosol prevention part 1070 is disposed so that the two side plates 373-1 and 373-2 for aerosol prevention part are respectively moved along the same vertical surfaces when the aerosol prevention part 1070 is moved down. Since the two side plates 373-1 and 373-2 for aerosol prevention part are respectively moved along the same vertical surfaces, the air flow generated by the movement of the two side plates 373-1 and 373-2 for aerosol prevention part is minimized.

Referring to FIGS. 12 and 13, the aerosol prevention part 1070 is installed so that upper inner surfaces of the two side plates 373-1 and 373-2 for aerosol prevention part are tightly contacted with the outer surface of the purification block 110 and lower ends thereof are inserted into the two insertion grooves (not shown) of the lower plate 351 for solution drip tray when the aerosol prevention part 1070 is moved down. Further, the aerosol prevention part 1070 is also installed so that both side ends of the two side plates 373-1 and 373-2 for aerosol prevention part are tightly contacted with the two side plates 353-1 and 353-2 for solution drip tray when the aerosol prevention part 1070 is moved down.

Sixth Embodiment

A sixth embodiment relates to yet another automatic purification apparatus for isolating target nucleic acids from a plurality of biological samples.

Referring to FIGS. 12 and 13, a solution drip tray and an aerosol prevention part of the sixth embodiment have the same structure as those of fifth embodiment. Therefore, the same reference numerals and technical terms are used for the same elements. In the sixth embodiment, the aerosol prevention part 1070 is fixedly installed at a vertical position in which an upper inner surface thereof can be tightly contacted with the outer surface of the purification block 110 when the purification block 110 is moved upward. Therefore, the sixth embodiment does not include the aerosol prevention part moving means for moving up and down the aerosol prevention part 1070. Further, unlike in the fifth embodiment, the lower plate 351 for solution drip tray is not formed with the two insertion grooves (not shown) which are formed in edge portions of an upper surface thereof. Thus, the lower plate 351 for solution drip tray of the sixth embodiment may be formed with a tightly-contacting plate equivalent to the tightly-contacting plates 53-1, 53-2, 55-1 and 55-2 for solution drip tray (referring to FIG. 5) of the first embodiment. The other matters are the same as in the fifth embodiment.

Seventh Embodiment

A seventh embodiment relates to yet another automatic purification apparatus for isolating target nucleic acids from a plurality of biological samples.

Figure 14:
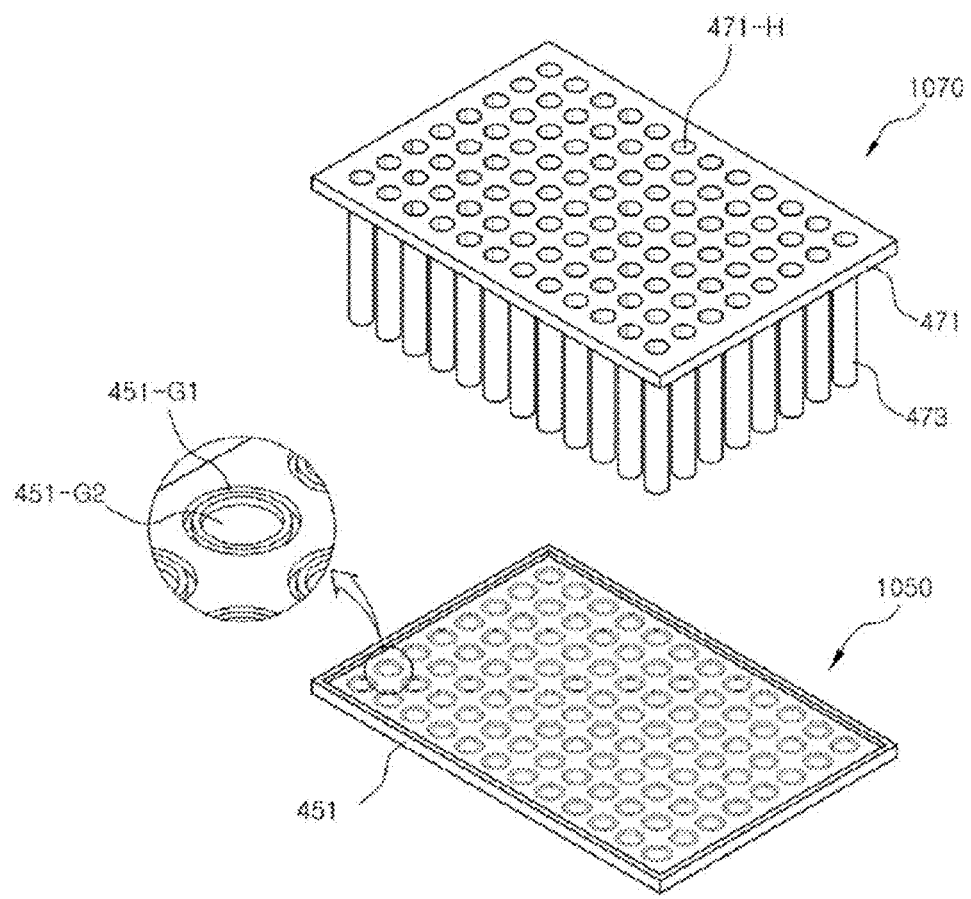
FIG. 14 is a perspective view of an aerosol prevention part and a solution drip tray according to a seventh embodiment of the present invention.

FIG. 14 is a perspective view of an aerosol prevention part and a solution drip tray according to a seventh embodiment of the present invention.

The seventh embodiment has the same structure as the second embodiment except the solution drip tray 1050 and the aerosol prevention part 1070. Therefore, the same reference numerals and technical terms are used for the same elements.

Referring to FIG. 14, the aerosol prevention part 1070 includes an aerosol prevention tube supporting plate 471 and an aerosol prevention tube 473.

Referring to FIG. 14, the aerosol prevention tube supporting plate 471 is formed with a plurality of through-holes 471-H which the plurality of pipettes P or the plurality of magnet tubes are inserted therein and passed therethrough. In order to enhance the airtightness, the plurality of through-holes 471-H may be formed to be slightly larger than the plurality of pipettes P or the plurality of magnet tubes, or may be formed to be contacted with the plurality of pipettes P or the plurality of magnet tubes and also to prevent the plurality of pipettes P or the plurality of magnet tubes from being separated downward when the aerosol prevention tube supporting plate 471 is moved. The aerosol prevention tube supporting plate 471 is fixedly connected to the lower portion of the second supporting part 186 for aerosol prevention part (referring to FIG. 8) and also located at a lower side of the purification block 110.

Referring to FIG. 14, the aerosol prevention tube 473 is provided in plural and also extended to a lower side of the aerosol prevention tube supporting plate 471. The plurality of aerosol prevention tubes 473 are communicated with the plurality of through-holes 471-H, and each lower end of the aerosol prevention tubes 473 is tightly contacted with the solution drip tray 1050. The plurality of aerosol prevention tubes 473 are formed so as to cover the portions of the plurality of pipettes P or the plurality of magnet rod tubes, which are smeared with a solution containing the target nucleic acid, when the aerosol prevention tube supporting plate 471 is moved down. The purification block 110 is repeatedly lifted up and down so that the plurality of pipettes P or the plurality of magnet tubes are repeatedly put in and out of solutions injected into multiple wells of a multi-well plate (now shown). Therefore, the aerosol prevention tube supporting plate 471 has to be further lifted down than a position of the purification block 110 which is lifted down in order to perform the target nucleic acid purification, thereby preventing a collision between the aerosol prevention tube supporting plate 471 and the purification block 110.

Referring to FIG. 14, the solution drip tray 1050 has a lower plate 451 for solution drip tray. The lower plate 451 for solution drip tray has a sufficient surface area in order to receive all of the solution drips from the plurality of pipettes P or the plurality of magnet rod tubes (not shown). An insertion groove 451-G1 in which the lower end of the aerosol prevention tube 473 is inserted is formed in an upper surface of the lower plate 451 for solution drip tray. Meanwhile, a solution collecting groove 451-G2 for receiving the solution drips may be formed inside the insertion groove 451-G1.

In the seventh embodiment, the portions of the plurality of pipettes P or the plurality of magnet rod tubes, which are smeared with a solution containing the target nucleic acid, are covered and shut off from the outside by the aerosol prevention tubes 473. In case that gaps among the plurality of pipettes P or the plurality of magnet rod tubes (not shown) are too small, it is difficult to insert the plurality of aerosol prevention tubes 473 onto the plurality of pipettes P or the plurality of magnet rod tubes (not shown). Therefore, the seventh embodiment can be applied only to a case that the plurality of pipettes P or the plurality of magnet rod tubes (not shown) are formed slimly so as to provide sufficient gaps among the plurality of pipettes P or the plurality of magnet rod tubes (not shown).

Eighth Embodiment

An eighth embodiment relates to yet another automatic purification apparatus for isolating target nucleic acids from a plurality of biological samples.

Referring to FIG. 14, a solution drip tray and an aerosol prevention part of the eighth embodiment have the same structure as those of seventh embodiment. Therefore, the same reference numerals and technical terms are used for the same elements. In the eighth embodiment, the aerosol prevention part 1070 is fixedly installed at a vertical position in which the plurality of aerosol prevention tubes 473 cover the portions of the plurality of pipettes P or the plurality of magnet rod tubes, which are smeared with a solution containing the target nucleic acid, when the purification block 110 is moved upward. Therefore, the eighth embodiment does not include the aerosol prevention part moving means for moving up and down the aerosol prevention part 1070. Further, unlike in the seventh embodiment, the lower plate 451 for solution drip tray is not formed with the insertion groove 451-G1. The other matters are the same as in the seventh embodiment.

Ninth Embodiment

A ninth embodiment relates to yet another automatic purification apparatus for isolating target nucleic acids from a plurality of biological samples.

Figure 15:
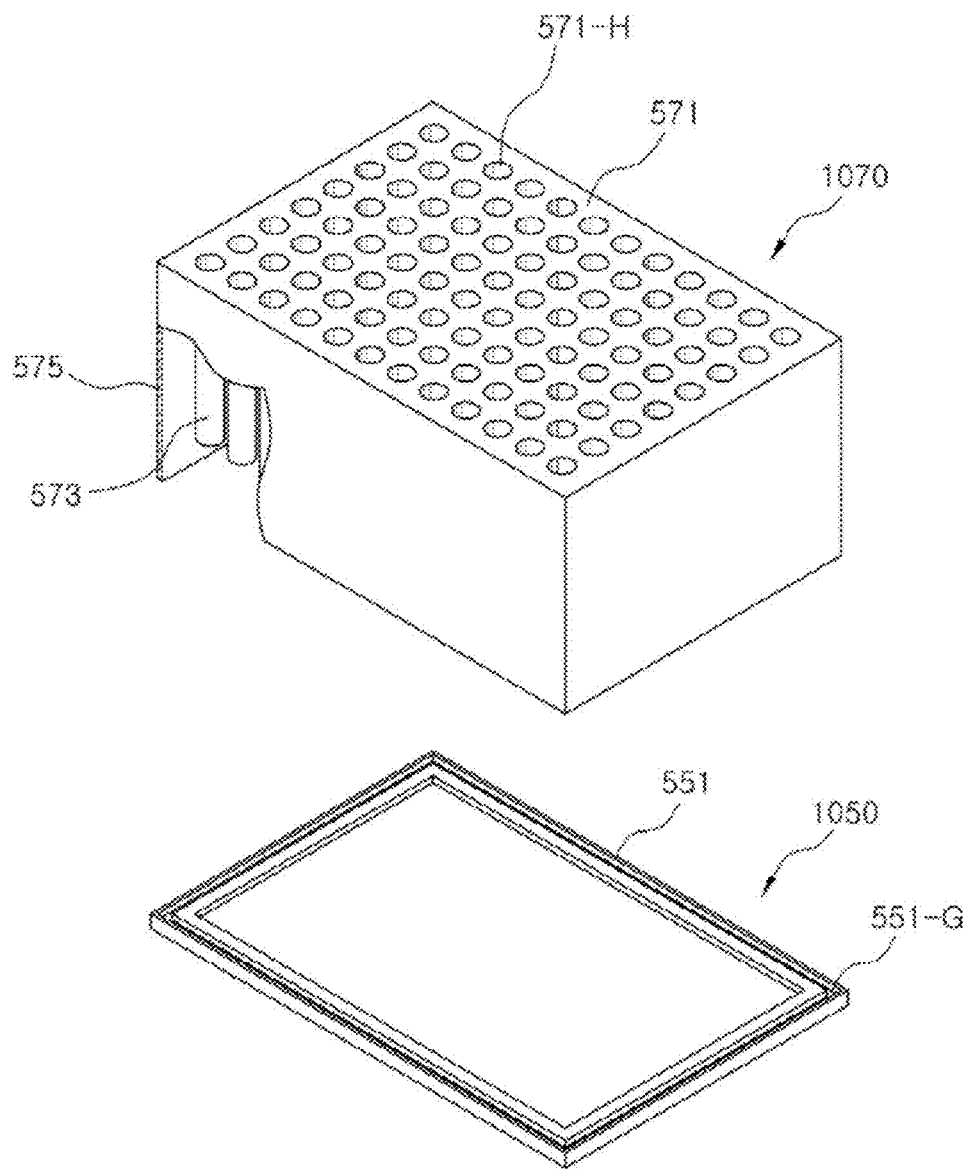
FIG. 15 is a perspective view of an aerosol prevention part and a solution drip tray according to a ninth embodiment of the present invention.

FIG. 15 is a perspective view of an aerosol prevention part and a solution drip tray according to a ninth embodiment of the present invention.

The ninth embodiment has the same structure as the second embodiment except the aerosol prevention part 1070.

Referring to FIG. 15, the aerosol prevention part 1070 includes an aerosol prevention tube supporting plate 571, an aerosol prevention tube 573 and an aerosol prevention container 575.

Referring to FIG. 15, the aerosol prevention tube supporting plate 571 is formed with a plurality of through-holes 571-H which the plurality of pipettes P or the plurality of magnet tubes are inserted therein and passed therethrough. The plurality of through-holes 571-H may have the same size as those of the seventh embodiment. The aerosol prevention tube supporting plate 571 is fixedly connected to the lower portion of the second supporting part 186 for aerosol prevention part (referring to FIG. 8).

Referring to FIG. 15, the aerosol prevention tube 573 is provided in plural and also extended to a lower side of the aerosol prevention tube supporting plate 571. The plurality of aerosol prevention tubes 573 are communicated with the plurality of through-holes 571-H. The plurality of aerosol prevention tubes 573 are formed so as to cover the portions of the plurality of pipettes P or the plurality of magnet rod tubes, which are smeared with a solution containing the target nucleic acid, when the aerosol prevention tube supporting plate 571 is moved down. In this case, like in the seventh embodiment, the aerosol prevention tube supporting plate 571 has to be further lifted down than a position of the purification block 110 which is lifted down in order to perform the target nucleic acid purification, thereby preventing a collision between the aerosol prevention tube supporting plate 571 and the purification block 110.

Referring to FIG. 15, the aerosol prevention container 575 is extended to a lower side of the aerosol prevention tube supporting plate 571 and also formed into a container shape for covering the plurality of aerosol prevention tubes 573. Meanwhile, the aerosol prevention container 575 is disposed so that a lower end thereof is tightly contacted with the solution drip tray 1050 when the aerosol prevention tube supporting plate 571 is moved down.

Referring to FIG. 15, the solution drip tray 1050 has a lower plate 551 for solution drip tray, like in the second embodiment. The lower plate 551 for solution drip tray has a sufficient surface area in order to receive all of the solution drips from the plurality of pipettes P or the plurality of magnet rod tubes (not shown). An insertion groove 551-G in which a lower end of the aerosol prevention container 575 is inserted when the aerosol prevention part 1070 is moved down is formed in an upper surface of the lower plate 551 for solution drip tray.

Like the seventh embodiment, the ninth embodiment can be applied only to a case that the plurality of pipettes P or the plurality of magnet rod tubes (not shown) are formed slimly so as to provide sufficient gaps among the plurality of pipettes P or the plurality of magnet rod tubes (not shown).

Tenth Embodiment

A tenth embodiment relates to yet another automatic purification apparatus for isolating target nucleic acids from a plurality of biological samples.

Referring to FIG. 15, a solution drip tray and an aerosol prevention part of the tenth embodiment have the same structure as those of ninth embodiment. Therefore, the same reference numerals and technical terms are used for the same elements. In the tenth embodiment, the aerosol prevention part 1070 is fixedly installed at a vertical position in which the plurality of aerosol prevention tubes 573 cover the portions of the plurality of pipettes P or the plurality of magnet rod tubes, which are smeared with a solution containing the target nucleic acid, when the purification block 110 is moved upward. Therefore, the tenth embodiment does not include the aerosol prevention part moving means for moving up and down the aerosol prevention part 1070. Further, the upper surface of the lower plate 551 for solution drip tray is not formed with the insertion groove 551-G. The other matters are the same as in the seventh embodiment.

Eleventh Embodiment

An eleventh embodiment relates to yet another automatic purification apparatus for isolating target nucleic acids from a plurality of biological samples.

Figure 16:
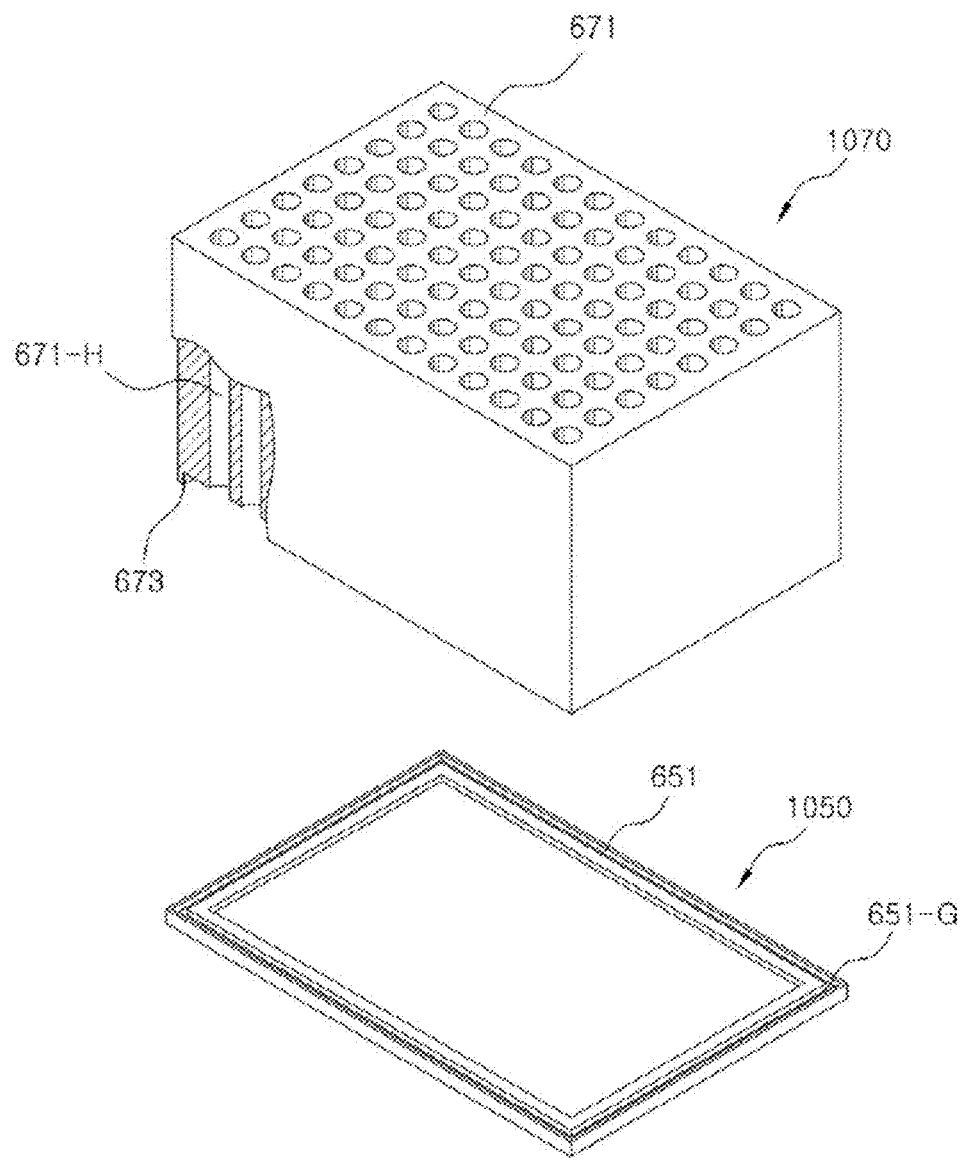
FIG. 16 is a perspective view of an aerosol prevention part and a solution drip tray according to an eleventh embodiment of the present invention.

FIG. 16 is a perspective view of an aerosol prevention part and a solution drip tray according to an eleventh embodiment of the present invention.

The eleventh embodiment has the same structure as the second embodiment except the aerosol prevention part 1070.

Referring to FIG. 16, the aerosol prevention part 1070 includes an aerosol prevention block 671 and an aerosol prevention container 673.

Referring to FIG. 16, the aerosol prevention block 671 is formed with a plurality of through-holes 671-H which the plurality of pipettes P or the plurality of magnet tubes are inserted therein and passed therethrough. Upper ends of the plurality of through-holes 671-H may have the same size as the plurality of through-holes 471-H of the seventh embodiment. Lower portions which are located below upper ends of the plurality of through-holes 671-H are formed so as to cover the portions of the plurality of pipettes P or the plurality of magnet rod tubes, which are smeared with a solution containing the target nucleic acid, when the aerosol prevention block 671 is moved down. In this case, like in the seventh embodiment, the aerosol prevention block 671 has to be further lifted down than a position of the purification block 110 which is lifted down in order to perform the target nucleic acid purification, thereby preventing a collision between the aerosol prevention block 671 and the purification block 110. The aerosol prevention block 671 is fixedly connected to the lower portion of the second supporting part 186 for aerosol prevention part (referring to FIG. 8) and located at a lower side of the purification block 110.

Referring to FIG. 16, the aerosol prevention container 673 is extended to a lower side of the aerosol prevention block 671 and formed into a container shape for surrounding positions which are located below the plurality of through-holes 671-H. Meanwhile, the aerosol prevention container 673 is disposed so that a lower end thereof is tightly contacted with the solution drip tray 1050 when the aerosol prevention block 671 is moved down.

Referring to FIG. 16, the solution drip tray 1050 has a lower plate 651 for solution drip tray. The lower plate 651 for solution drip tray has a sufficient surface area in order to receive all of the solution drips from the plurality of pipettes P or the plurality of magnet rod tubes (not shown). An insertion groove 651-G in which a lower end of the aerosol prevention container 673 is inserted when the aerosol prevention part 1070 is moved down is formed in an upper surface of the lower plate 651 for solution drip tray.

Like the seventh embodiment, the eleventh embodiment can be applied only to a case that the plurality of pipettes P or the plurality of magnet rod tubes (not shown) are formed slimly so as to provide sufficient gaps among the plurality of pipettes P or the plurality of magnet rod tubes (not shown).

Twelfth Embodiment

A twelfth embodiment relates to yet another automatic purification apparatus for isolating target nucleic acids from a plurality of biological samples.

Referring to FIG. 16, a solution drip tray and an aerosol prevention part of the twelfth embodiment have the same structure as those of eleventh embodiment. Therefore, the same reference numerals and technical terms are used for the same elements. In the twelfth embodiment, the aerosol prevention part 1070 is fixedly installed at a vertical position in which the plurality of through-holes 671-H cover the portions of the plurality of pipettes P or the plurality of magnet rod tubes, which are smeared with a solution containing the target nucleic acid, when the purification block 110 is moved upward. Therefore, the twelfth embodiment does not include the aerosol prevention part moving means for moving up and down the aerosol prevention part 1070. Further, the lower plate 651 for solution drip tray is not formed with the insertion groove 651-G. The other matters are the same as in the eleventh embodiment.

Thirteenth Embodiment

A thirteenth embodiment relates to yet another automatic purification apparatus for isolating target nucleic acids from a plurality of biological samples.

Figure 17:
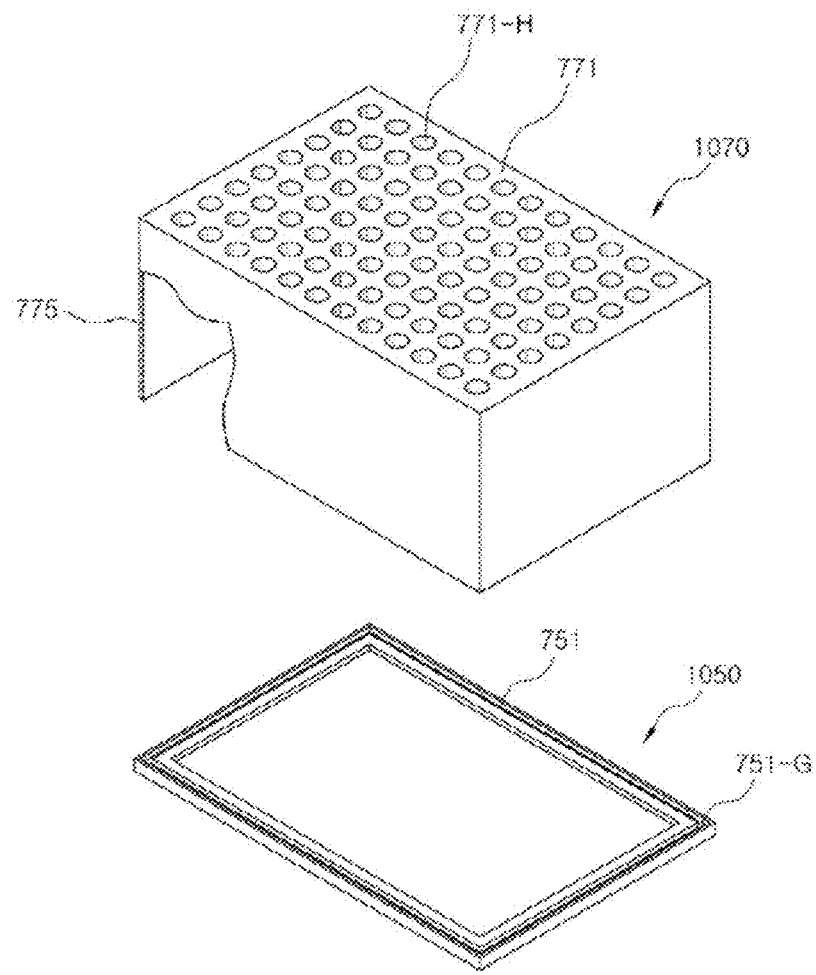
FIG. 17 is a perspective view of an aerosol prevention part and a solution drip tray according to a thirteenth embodiment of the present invention.

FIG. 17 is a perspective view of an aerosol prevention part and a solution drip tray according to a thirteenth embodiment of the present invention.

The thirteenth embodiment has the same structure as the second embodiment except the aerosol prevention part 1070.

Referring to FIG. 17, the aerosol prevention part 1070 includes an upper plate 771 for aerosol prevention part and an aerosol prevention container 775.

Referring to FIG. 17, the upper plate 771 for aerosol prevention part is formed with a plurality of through-holes 771-H which the plurality of pipettes P or the plurality of magnet tubes are inserted therein and passed therethrough. The plurality of through-holes 771-H may have the same size as the plurality of through-holes 471-H of the seventh embodiment. The upper plate 771 for aerosol prevention part is fixedly connected to the lower portion of the second supporting part 186 for aerosol prevention part (referring to FIG. 8) and located at a lower side of the purification block 110.

Referring to FIG. 17, the aerosol prevention container 775 is extended from an edge portion of the upper plate 771 for aerosol prevention part to a lower side thereof and also formed into a container shape so as to cover the portions of the plurality of pipettes P or the plurality of magnet rod tubes, which are smeared with a solution containing the target nucleic acid, when the upper plate 771 for aerosol prevention part is moved down. Meanwhile, the aerosol prevention container 775 is disposed so that a lower end thereof is tightly contacted with the solution drip tray 1050 when the upper plate 771 for aerosol prevention part is moved down. In this case, like in the seventh embodiment, the upper plate 771 for aerosol prevention part has to be further lifted down than a position of the purification block 110 which is lifted down in order to perform the target nucleic acid purification, thereby preventing a collision between the upper plate 771 for aerosol prevention part and the purification block 110.

Referring to FIG. 17, the solution drip tray 1050 has a lower plate 751 for solution drip tray, like in the second embodiment. The lower plate 751 for solution drip tray has a sufficient surface area in order to receive all of the solution drips from the plurality of pipettes P or the plurality of magnet rod tubes (not shown). An insertion groove 751-G in which a lower end of the aerosol prevention container 775 is inserted when the aerosol prevention part 1070 is moved down is formed in an upper surface of the lower plate 751 for solution drip tray.

Like the seventh embodiment, the thirteenth embodiment can be applied only to a case that the plurality of pipettes P or the plurality of magnet rod tubes (not shown) are formed slimly so as to provide sufficient gaps among the plurality of pipettes P or the plurality of magnet rod tubes (not shown).

Fourteenth Embodiment

A fourteenth embodiment relates to yet another automatic purification apparatus for isolating target nucleic acids from a plurality of biological samples.

Referring to FIG. 17, a solution drip tray and an aerosol prevention part of the fourteenth embodiment have the same structure as the solution drip tray 1050 and the aerosol prevention part 1070 of thirteenth embodiment. Therefore, the same reference numerals and technical terms are used for the same elements. In the fourteenth embodiment, the aerosol prevention part 1070 is fixedly installed at a vertical position in which the aerosol prevention container 775 covers the portions of the plurality of pipettes P or the plurality of magnet rod tubes, which are smeared with a solution containing the target nucleic acid, when the purification block 110 is moved upward. Therefore, the fourteenth embodiment does not include the aerosol prevention part moving means for moving up and down the aerosol prevention part 1070. Further, the lower plate 751 for solution drip tray is not formed with the insertion groove 751-G. The other matters are the same as in the seventh embodiment.

Fifteenth Embodiment

A fifteenth embodiment relates to an automatic purification method of isolating target nucleic acids from a plurality of biological samples.

Figure 18:
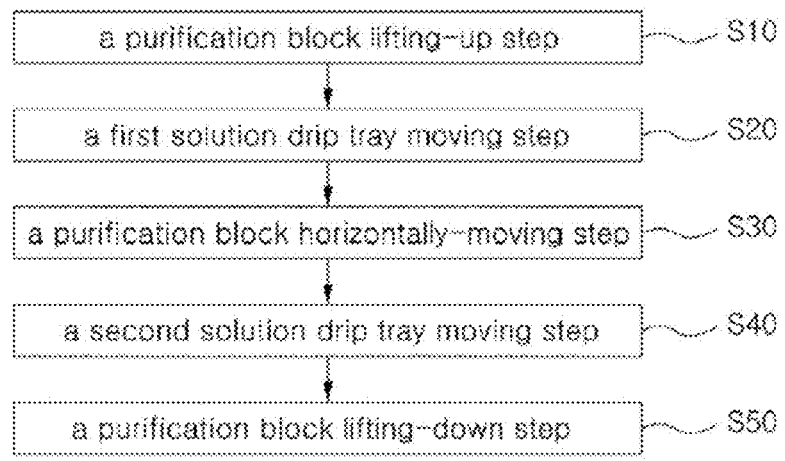
FIG. 18 is a flow chart of a fifteenth embodiment of the present invention.

FIG. 18 is a flow chart of a fifteenth embodiment of the present invention.

The fifteenth embodiment is characterized in that, when the purification block 110 in which the plurality of pipettes P or the plurality of magnet rod tubes are installed is moved horizontally, the portions of the plurality of pipettes P or the plurality of magnet rod tubes, which are smeared with a solution containing the target nucleic acid, are maintained in a state of being shut off from the outside.

Hereinafter, the automatic purification method of the fifteenth embodiment will be described using the embodiment in which the aerosol prevention part 1070 is fixed to the certain vertical position.

Referring to FIG. 18, the fifteenth embodiment includes a purification block lifting-up step S10, a first solution drip tray moving step S20, a purification block horizontally-moving step S30, a second solution drip tray moving step S40 and a purification block lifting-down step S50.

Referring to FIGS. 1 to 5, in the purification block lifting-up step S10, the purification block 110 is moved upward so that the lower ends of the plurality of pipettes P or the plurality of magnet rod tubes installed in the purification block 110 are located at an upper side of the lower end of the aerosol prevention part 1070 which is fixed to the certain vertical position. The purification block 110 is repeatedly lifted up and down so that the plurality of pipettes P or the plurality of magnet tubes are repeatedly put in and out of solutions injected into multiple wells of a multi-well plate (now shown). In other words, the lower ends of the plurality of pipettes P or the plurality of magnet rod tubes are located at the upper side of the lower end of the aerosol prevention part 1070 through the purification block lifting-up step S10.

Referring to FIG. 1, in the first solution drip tray moving step S20, the solution drip tray 1050 for receiving the solution drips from the plurality of pipettes P or the plurality of magnet tubes is moved so as to be tightly contacted with the lower end of the aerosol prevention part 1070 and then to cover the portions of the plurality of pipettes P or the plurality of magnet rod tubes, which are smeared with a solution containing the target nucleic acid, together with the aerosol prevention part 1070. Thus, when the purification block 110 is moved horizontally, the solution drips from the plurality of pipettes P or the plurality of magnet rod tubes are not fallen into the multi-well plate (not shown) which is located at a lower side of the plurality of pipettes P or the plurality of magnet rod tubes, but received in the solution drip tray 1050. Therefore, it is prevented that the solution smeared on the plurality of pipettes P or the plurality of magnet rod tubes is undesirably injected into the wells of the multi-well plate (not shown). Further, the aerosol prevention part 1070 is tightly contacted with the solution drip tray 1050 moved through the first solution drip tray moving step S20 so that the portions of the plurality of pipettes P or the plurality of magnet rod tubes, which are smeared with a solution containing the target nucleic acid, are shut off from the outside.

Referring to FIGS. 1 to 30, in the first solution drip tray moving step S20, the lower plate 51 for solution drip tray is moved along the same horizontal plane so as to minimize the air flow generated by the solution drip tray 1050.

In the purification block horizontally-moving step S30, the purification block 110 is moved horizontally in a state that the portions of the plurality of pipettes P or the plurality of magnet rod tubes, which are smeared with a solution containing the target nucleic acid, are shut off from the outside. Therefore, it is prevented that the aerosol is generated from the solution containing the target nucleic acid, which is smeared on the circumferential surface of one of the plurality of pipettes P or the plurality of magnet rod tubes, when the purification block 110 is moved horizontally, and then attached to the circumferential surfaces of another pipettes P or another magnet rod tubes.

Referring to FIGS. 1 and 2, in the second solution drip tray moving step S40, the solution drip tray 1050 is moved to a position that can avoid in contact with the plurality of pipettes P or the plurality of magnet rod tubes (not shown) when the purification block 110 is moved down. In the second solution drip tray moving step S40, the lower plate 51 for solution drip tray is moved along the same horizontal plane so as to minimize the air flow generated by the solution drip tray 1050, like in the first solution drip tray moving step S20.

Referring to FIG. 3, in purification block lifting-down step S50, the purification block 110 is moved down so that the plurality of pipettes P or the plurality of magnet rod tubes are put in nucleic acid extract solutions injected into the multiple wells of the multi-well plate (not shown).

Sixteenth Embodiment

A sixteenth embodiment relates to another automatic purification method of isolating target nucleic acids from a plurality of biological samples.

Figure 19:
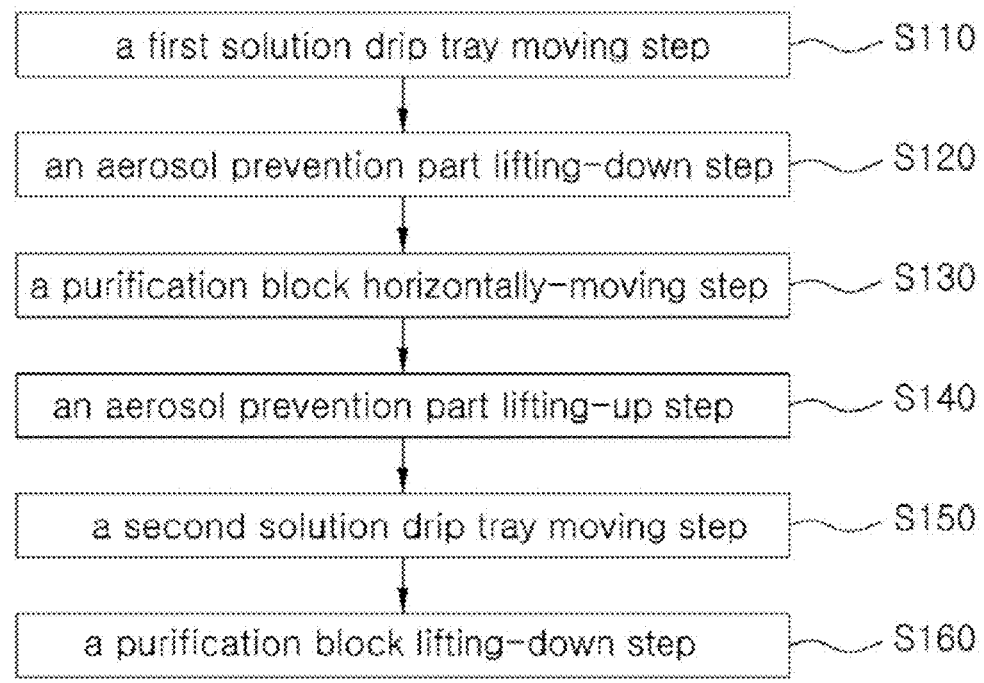
FIG. 19 is a flow chart of a sixteenth embodiment of the present invention.

FIG. 19 is a flow chart of a sixteenth embodiment of the present invention.

The sixteenth embodiment is characterized in that, when the purification block 110 in which the plurality of pipettes P or the plurality of magnet rod tubes are installed is moved horizontally, the portions of the plurality of pipettes P or the plurality of magnet rod tubes, which are smeared with a solution containing the target nucleic acid, are maintained in a state of being shut off from the outside.

Hereinafter, the automatic purification method of the fifteenth embodiment will be described using the embodiment in which the aerosol prevention part 1070 is installed so as to be movable up and down.

Referring to FIG. 19, the sixteenth embodiment includes a first solution drip tray moving step S110, an aerosol prevention part lifting-down step S120, a purification block horizontally-moving step S130, an aerosol prevention part lifting-up step S140, a second solution drip tray moving step S150 and a purification block lifting-down step S160.

Referring to FIGS. 8 and 9, in the first solution drip tray moving step S110, the solution drip tray 1050 is moved to the lower side of the plurality of pipettes P or the plurality of magnet tubes installed in the purification block 110. Thus, when the purification block 110 is moved horizontally, the solution drips from the plurality of pipettes P or the plurality of magnet rod tubes are not fallen into the multi-well plate (not shown) which is located at a lower side of the plurality of pipettes P or the plurality of magnet rod tubes, but received in the solution drip tray 1050. Therefore, it is prevented that the solution smeared on the plurality of pipettes P or the plurality of magnet rod tubes is undesirably injected into the wells of the multi-well plate (not shown).

Referring to FIGS. 8 and 9, in the first solution drip tray moving step S110, the lower plate 51 for solution drip tray is moved along the same horizontal plane so as to minimize the air flow generated by the solution drip tray 1050.

Further, referring to FIGS. 10 to 13, in the first solution drip tray moving step S110, the side plates 253, 353-1 and 353-2 for solution trip tray are moved along the same vertical surfaces so as to minimize the air flow generated by the solution drip tray 1050.

Referring to FIGS. 8 and 9, in the aerosol prevention part lifting-down step S120, the aerosol prevention part 1070 is moved in a down direction of the purification block 110. Thus, the aerosol prevention part 1070 is tightly contacted with the solution drip tray 1050 through the first solution drip tray moving step S110 so that the portions of the plurality of pipettes P or the plurality of magnet rod tubes, which are smeared with a solution containing the target nucleic acid, are shut off from the outside. The purification block 110 is repeatedly lifted up and down so that the plurality of pipettes P or the plurality of magnet tubes are repeatedly put in and out of solutions injected into multiple wells of a multi-well plate (now shown). FIG. 8 shows a state before the purification block 110 is initially lifted down.

In the purification block horizontally-moving step S130, the purification block 110 is moved horizontally in the state that the portions of the plurality of pipettes P or the plurality of magnet rod tubes, which are smeared with the solution containing the target nucleic acid, are shut off from the outside, and thus the air flow is not generated around the portions of the plurality of pipettes P or the plurality of magnet rod tubes, which are smeared with a solution containing the target nucleic acid. Therefore, it is prevented that the aerosol is generated from the solution containing the target nucleic acid, which is smeared on the circumferential surface of one of the plurality of pipettes P or the plurality of magnet rod tubes, when the purification block 110 is moved horizontally, and then attached to the circumferential surfaces of another pipettes P or another magnet rod tubes.

In the aerosol prevention part lifting-up step S140, the aerosol prevention part 1070 is moved in the upper direction of the purification block 110 so that the lower end of the aerosol prevention part 1070 is separated from the insertion groove 151-G (referring to FIG. 8) of the solution drip tray 1050. In the aerosol prevention part lifting-up step S140, the aerosol prevention part 1070 is slightly moved upward so that the lower end thereof is separated from the insertion groove 151-G of the solution drip tray 1050. Meanwhile, if an (n+1)th aerosol prevention part lifting-down step S120 is performed after the nth aerosol prevention part lifting-up step S140, the plurality of pipettes P or the plurality of magnet rod tubes are smeared with the solution containing the target nucleic acid or other solutions. Therefore, when the (n+1)th aerosol prevention part lifting-down step S120 is performed and thus the aerosol prevention part 1070 is moved down, it is preferable that the air flow is not generated. In the aerosol prevention part lifting-up step S140, the lower end of the aerosol prevention part 1070 is slightly moved up so as to be separated from the insertion groove 151-G of the solution drip tray 1050, and thus in the (n+1)th aerosol prevention part lifting-down step S120, when the aerosol prevention part 1070 as shown in FIGS. 14 to 17 is moved downward, the air flow is hardly generated.

Referring to FIG. 8, in the second solution drip tray moving step S150, the solution drip tray 1050 is moved to a position that can avoid in contact with the plurality of pipettes P or the plurality of magnet rod tubes (not shown) when the purification block 110 is moved down. In the second solution drip tray moving step S150, the lower plate 151 for solution drip tray is moved along the same horizontal plane so as to minimize the air flow generated by the solution drip tray 1050, like in the first solution drip tray moving step S110.

In the purification block lifting-down step S160, the purification block 110 is moved down so that the plurality of pipettes P or the plurality of magnet rod tubes are put in nucleic acid extract solutions injected into the multiple wells of the multi-well plate (not shown).

INDUSTRIAL APPLICABILITY

According to the present invention as described above, since the pipette or the magnet rod tube is moved only when it is closed so as to be shut off from the outside and then the nucleic acid purification is performed, it is fundamentally prevented that the aerosol is generated due to the vortex of air while the pipette or the magnet rod tube is moved horizontally. Further, since the vortex of air is not generated when the purification block having the plurality of pipettes or the plurality of magnet rod tubes is moved horizontally, the generation of aerosol and the cross pollution are fundamentally prevented.

Further, according to the present invention, it is fundamentally prevented that the plurality of unit wells of the multi-well plate are polluted by the undesirable solution drips from the plurality of pipettes or the plurality of magnet rod tubes.

While the present invention has been described with respect to the specific embodiments, it will be apparent to those skilled in the art that various changes and modifications may be made without departing from the spirit and scope of the invention as defined in the following claims.

The invention claimed is:

1. An automatic purification apparatus for isolating target nucleic acids from a plurality of biological samples, comprising:
    a purification block 110 moving vertically and horizontally, wherein a plurality of pipettes P or a plurality of magnet rod tubes are installed in the purification block 110;
    a solution drip tray 1050 disposed apart from lower ends of the plurality of pipettes P or the plurality of magnet rod tubes, wherein the solution drip tray 1050 is movable to a first position where the solution drip tray 1050 can receive solution drips from the plurality of pipettes P or the plurality of magnet rod tubes and a second position where the solution drip tray 1050 can avoid in contact with plurality of pipettes P or the plurality of magnet rod tubes when the purification block 110 is moved down; and
    an aerosol prevention part 1070 which is disposed on an outer surface of the purification block 110 and vertically movable with respect to the purification block along the outer surface of the purification block,
    wherein the aerosol prevention part 1070 moves downward so that an end portion of the aerosol prevention part 1070 is tightly contacted with the solution drip tray 1050 to cover smeared portions of the plurality of pipettes P or the plurality of magnet rod tubes when the solution drip tray moves to the first position,
    wherein the smeared portions of the plurality of pipettes P or the plurality of magnet rod tubes are smeared with a solution containing the target nucleic acid, so that the portions of the plurality of pipettes P or the plurality of magnet rod tubes are covered from the outside.

2. The automatic purification apparatus of claim 1, wherein the aerosol prevention part 1070 has a rectangular box shape and comprises a first side plate 73-1, a third side plate 73-2 for aerosol prevention part facing the first side plate 73-1, a second side plate 75-1 of which both side ends are connected with the first and third side plates 73-1 and 73-2, and a fourth side plate 75-2 facing the second side plate 75-1, of which both side ends are connected with the first and third side plates 73-1 and 73-2 and wherein a lower end of the fourth side plate 75-2 is located at higher position than a lower end of the second side plate 75-1, and
    the solution drip tray 1050 comprises a lower plate 51, a first tightly-contacting plate 53-1 extended upwardly from the lower plate 51 and tightly contacting an outer surface of a lower portion of the first side plate 73-1 when the solution drip tray 1050 moves to the first position, a second tightly-contacting plate 55-1 extended upwardly from the lower plate 51 and tightly contacting an inner surface of a lower portion of the second side plate 75-1 when the solution drip tray 1050 moves to the first position, a third tightly-contacting plate 53-2 extended upwardly from the lower plate 51 and tightly contacting an outer surface of a lower portion of the third side plate 73-2 when the solution drip tray 1050 moves to the first position, and a fourth tightly-contacting plate 55-2 extended upwardly from the lower plate 51 and tightly contacting an inner surface of a lower portion of the second side plate 75-2 when the solution drip tray 1050 moves to the first position.

3. The automatic purification apparatus of claim 1, wherein the solution drip tray 1050 has a flat plate shape, and the aerosol prevention part 1070 has a box shape and disposed to be moved to up and down directions of the purification block 110, such that an upper inner surface thereof is tightly contacted with the purification block 110 and a lower end thereof is tightly contacted with the solution drip tray 1050 when the aerosol prevention part 1070 moves to the first position.

4. The automatic purification apparatus of claim 1, wherein the solution drip tray 1050 comprises a lower plate 251 and a side plate 253 extended from an edge portion of the lower plate 251,
    the aerosol prevention part 1070 is disposed on the outer surface of the purification block 110 and vertically movable along the outer surface of the purification block, and
    an upper inner surface of the aerosol prevention part 1070 is tightly contacted with the OUTER surface of the purification block 110 and a lower end of the aerosol prevention part 1070 is tightly contacted with the solution drip tray 1050 when the aerosol prevention part 1070 moves to the first position.

5. The automatic purification apparatus of claim 1, wherein the solution drip tray 1050 comprises a lower plate 251 and a side plate 253 extended from an edge portion of the lower plate 251,
    the aerosol prevention part 1070 is disposed on the outer surface of the purification block 110 and vertically movable along the outer surface of the purification block, and
    an upper inner surface of the aerosol prevention part 1070 is tightly contacted with the outer surface of the purification block 110 and a lower end of the aerosol prevention part 1070 is tightly contacted with the lower plate for solution drip tray and both side ends of an opened circumferential surface thereof are tightly contacted with the side plate 253, when the purification block 110 moves to the first position.

6. The automatic purification apparatus of claim 1, wherein the solution drip tray 1050 comprises a lower plate 351, a first side plate 353-1 extended from a first edge portion of the lower plate 351, and a second side plate 353-2 extended from a second edge portion of the lower plate 351, wherein the first edge portion and the second edge portion face each other, and
    the aerosol prevention part 1070 is disposed on the outer surface of the purification block 110 and vertically movable along the outer surface of the purification block, and comprises a first side plate 373-1 and a second side plate 373-2 facing the first side plate 373-1, wherein both of the first and second side plates 373-1 and 373-2 are expanded perpendicular to the first and second side plates 353-1 and 353-2,
    upper inner surfaces of the aerosol prevention part 1070 are tightly contacted with the outer surface of the purification block 110, lower ends of the aerosol prevention part 1070 are tightly contacted with the lower plate 351, and both edges of the first and second side plates 373-1 and 373-2 of the aerosol prevention part 101 are tightly contacted with the first and second side plates 353-1 and 353-2, when the aerosol prevention part 1070 moves to the first position.

7. The automatic purification apparatus of claim 1, wherein the solution drip tray 1050 comprises a lower plate 351, a first side plate 353-1 extended from a first edge portion of the lower plate 351 and a second side plate 353-2 extended from a second edge portion of the lower plate 351, wherein both of the first and second side plates 373-1 and 373-2 are expanded perpendicular to the first and second side plate 353-1 and 353-2, the aerosol prevention part 1070 is disposed on the outer surface of the purification block 110 and vertically movable along the outer surface of the purification block, and upper inner surfaces of the aerosol prevention part 1070 are tightly contacted with the outer surface of the purification block 110, lower ends of the aerosol prevention part 1070 are tightly contacted with the lower plate 351, and both edges of the first and second side plates 373-1 and 373-2 of the aerosol prevention part 1070 are tightly contacted with the first and second the side plates 353-1 and 353-2, when the purification block 110 moves to the first position.

8. The automatic purification apparatus of claim 3, wherein the solution drip tray 1050 comprises an insertion groove 151-G in which a lower end of the aerosol prevention part 1070 is inserted.

9. The automatic purification apparatus of claim 1, wherein the solution drip tray 1050 has a flat plate shape, the aerosol prevention part 1070 is disposed at a lower side of the purification block 110 so as to be moved to up and down directions of the purification block 110, and the aerosol prevention part 1070 comprises an aerosol prevention tube supporting plate 471 having a plurality of through-holes 471-H, a plurality of pipettes P or a plurality of magnet rod tubes inserted in and passed through the plurality of through-holes, and a plurality of aerosol prevention tubes 473 each of which is connected to the plurality of through-holes 471-H to cover the smeared portions of the plurality of pipettes P or the plurality of magnet rod tubes when the aerosol prevention tube supporting plate 471 is moved down.

10. The automatic purification apparatus of claim 1, wherein the aerosol prevention part 1070 further comprises an aerosol prevention container 575 which is extended downwardly from the edges of the aerosol prevention tube supporting plate 571 to cover the plurality of aerosol prevention tubes 573, wherein a lower end of the aerosol prevention container 575 is tightly contacted with the solution drip tray 1050 when the aerosol prevention tube supporting plate 571 is moved down.

11. The automatic purification apparatus of claim 1, wherein the solution drip tray 1050 has a flat plate shape, the aerosol prevention part 1070 is disposed surrounding an outer portion of the purification block 110 and is movable in a vertical direction along the purification block, and the aerosol prevention part 1070 comprises an aerosol prevention block 671 having a plurality of through-holes 671-H to cover the smeared portions of the plurality of pipettes P or the plurality of magnet rod tubes when the aerosol prevention block 671 is moved down.

12. The automatic purification apparatus of claim 1, wherein the solution drip tray 1050 has a flat plate shape, the aerosol prevention part 1070 is disposed surrounding an outer portion of the purification block 110 and is movable in a vertical direction along the purification block, and the aerosol prevention part 1070 comprises an upper plate 771 having a plurality of through-holes 771-H, a plurality of pipettes P or a plurality of magnet rod tubes inserted in and passed through the plurality of through-holes, and an aerosol prevention container 775 which is extended from an edge portion of the upper plate 771 to cover the smeared portions of the plurality of pipettes P or the plurality of magnet rod tubes when the upper plate 771 is moved down, wherein a lower end of the aerosol prevention container 775 is tightly contacted with the solution drip tray 1050 when the solution drip tray 1050 moves to the first direction.

* * * * *